(12) United States Patent
Nakamura et al.

(10) Patent No.: US 8,075,477 B2
(45) Date of Patent: Dec. 13, 2011

(54) ELECTRIC CONNECTOR FOR ENDOSCOPE, ENDOSCOPE, AND METHOD FOR ASSEMBLING ELECTRIC CONNECTOR

(75) Inventors: Naohiro Nakamura, Hachioji (JP); Shiori Kuwahara, Hachioji (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 1025 days.

(21) Appl. No.: 11/827,752

(22) Filed: Jul. 13, 2007

(65) Prior Publication Data

US 2008/0249363 A1    Oct. 9, 2008

Related U.S. Application Data

(63) Continuation of application No. PCT/JP2006/300459, filed on Jan. 16, 2006.

(30) Foreign Application Priority Data

Jan. 17, 2005    (JP) .................................. 2005-009476
Apr. 8, 2005     (JP) .................................. 2005-112459

(51) Int. Cl.
    *A61B 1/00*       (2006.01)
(52) U.S. Cl. ............................ 600/132; 600/130; 439/67
(58) Field of Classification Search .................. 600/109, 600/110, 132, 130; 439/55, 65, 67, 77, 660
    See application file for complete search history.

(56) References Cited

U.S. PATENT DOCUMENTS

| | | | |
|---|---|---|---|
| 4,708,126 A * | 11/1987 | Toda et al. ..................... | 600/132 |
| 4,811,107 A | 3/1989 | Bridges et al. | |
| 5,001,420 A * | 3/1991 | Germer et al. ................ | 324/142 |
| 5,239,983 A * | 8/1993 | Katsurada ..................... | 600/178 |
| 5,609,561 A * | 3/1997 | Uehara et al. ................. | 600/112 |
| 5,702,345 A * | 12/1997 | Wood et al. .................... | 600/109 |
| 5,957,727 A * | 9/1999 | Page, Jr. .................... | 439/607.58 |
| 6,002,437 A | 12/1999 | Morioka et al. | |
| 6,293,910 B1 * | 9/2001 | Yamakita et al. ............. | 600/132 |
| 7,300,397 B2 * | 11/2007 | Adler et al. .................... | 600/110 |
| 7,641,610 B2 * | 1/2010 | Nakamura et al. ............ | 600/132 |
| 2005/0112910 A1 * | 5/2005 | Randall et al. ................. | 439/62 |
| 2006/0287576 A1 * | 12/2006 | Tsuji et al. .................... | 600/132 |
| 2007/0038024 A1 * | 2/2007 | Nakamura et al. ............ | 600/110 |

FOREIGN PATENT DOCUMENTS

JP         05-021927         1/1993

(Continued)

OTHER PUBLICATIONS

Abstract of Japanese Patent Application Publication No. 02-129872, published May 17, 1990. Extended Supplementary European Search Report dated Feb. 17, 2010.
English Abstract only of WO 2004/040700 A2, May 2004.

*Primary Examiner* — John P Leubecker
(74) *Attorney, Agent, or Firm* — Scully, Scott, Murphy & Presser, P.C.

(57) ABSTRACT

An electric connector for an endoscope, an endoscope, and a method for assembling an electric connector which make it possible to simplify work operations such as operation checks and repairs of the endoscope, as well as to reduce the time for the work operations. An endoscope having an insertion portion, an operation portion provided at a proximal end portion of the insertion portion, and a connection cable connected to the operation portion and having an electric connector at a proximal end thereof. The endoscope has a cable wire which is inserted through the endoscope and extends from the electric connector toward a distal end and a connector to which an end portion of the cable wire is releasably connected.

16 Claims, 16 Drawing Sheets

FOREIGN PATENT DOCUMENTS

| | | |
|---|---|---|
| JP | 08-222294 | 8/1996 |
| JP | 09-294714 | 11/1997 |
| JP | 10-005175 | 1/1998 |
| JP | 10-014867 | 1/1998 |
| JP | 2902654 | 3/1999 |
| JP | 2000-113933 | 4/2000 |
| JP | 2001-068184 | 3/2001 |
| JP | 2003-190085 | 7/2003 |
| JP | 2004-095246 | 3/2004 |
| JP | 2006-505107 | 2/2006 |

\* cited by examiner

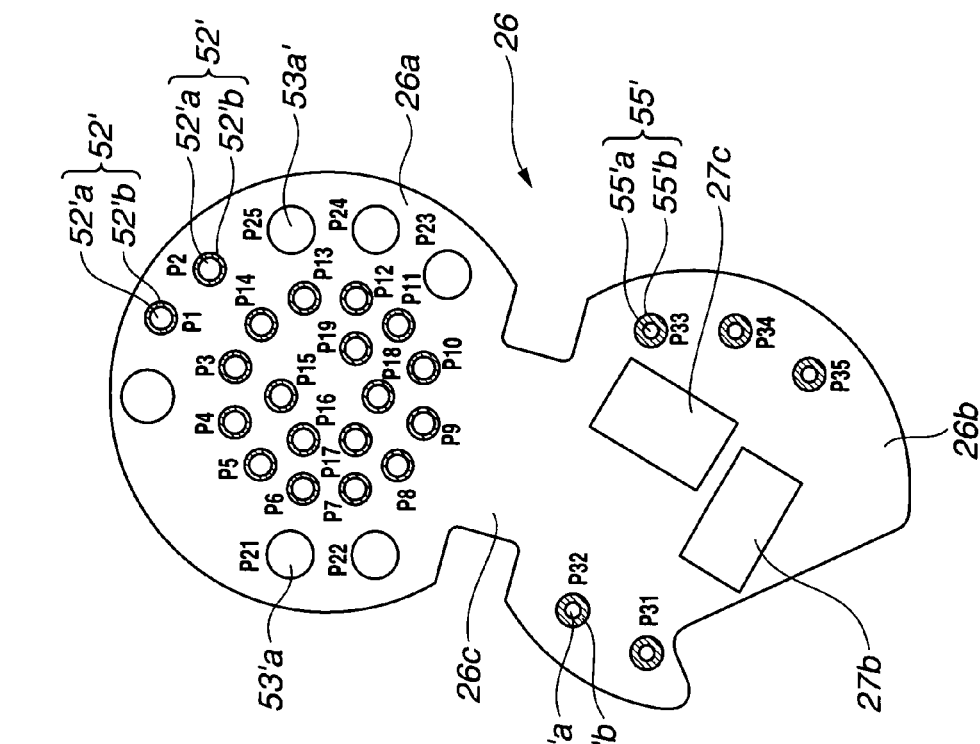
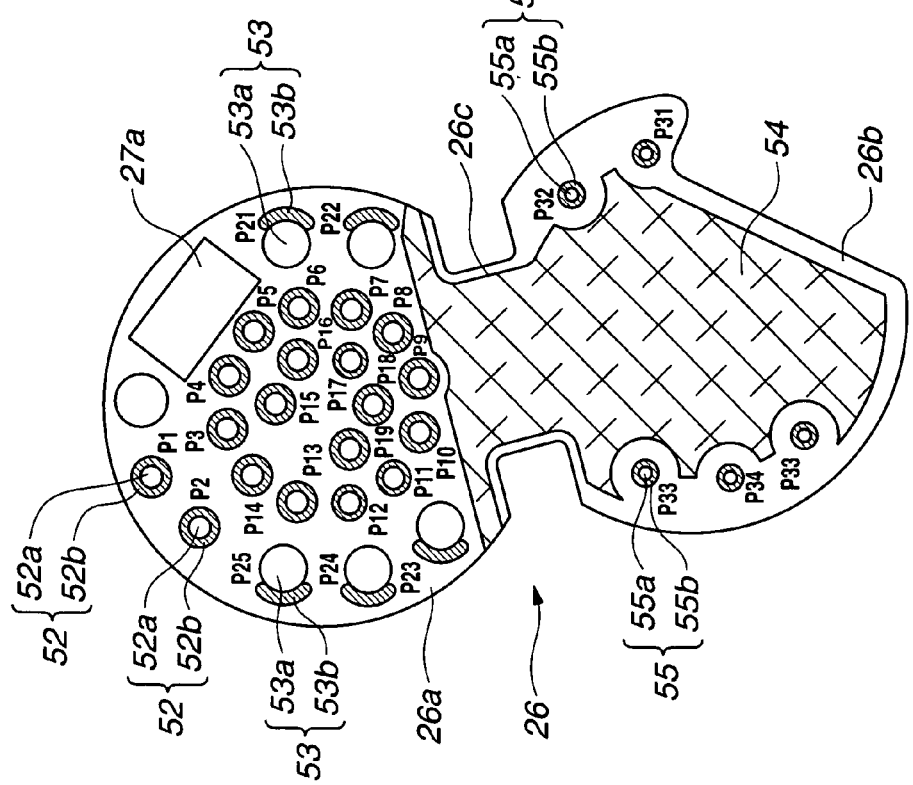

Prior Art

ELECTRIC CONNECTOR FOR ENDOSCOPE, ENDOSCOPE, AND METHOD FOR ASSEMBLING ELECTRIC CONNECTOR

CROSS REFERENCE TO RELATED APPLICATION

This application is a continuation application of PCT/JP2006/300459 filed on Jan. 16, 2006 and claims the benefit of Japanese Applications No. 2005-009476 filed in Japan on Jan. 17, 2005 and No. 2005-112459 filed in Japan on Apr. 8, 2005, the entire contents of each of which are incorporated herein by their reference.

BACKGROUND OF THE INVENTION

1. Field of the Invention

The present invention relates to an electric connector for an endoscope that connects the endoscope to an external instrument to be combined with the endoscope for use, an endoscope, and a method for assembling the electric connector.

2. Description of the Related Art

An electric connector to which a plurality of cable wires are connected is generally used to electrically connect various electronic instruments together. An electronic endoscope apparatus, an electronic instrument in medical fields, has an electronic endoscope containing a solid image pickup device (hereinafter simply referred to as a CCD) that is inserted into the body cavity to pick up images of the body cavity, and a video processor as an external instrument that executes predetermined signal processing on image pickup signals obtained by the electronic endoscope to generate endoscope video signals. The electronic endoscope and the video processor are connected together by an electric connector to which a plurality of cable wires for the transmission and reception of various signals and the supply of driving power are connected.

For example, Japanese Patent No. 2902654 proposes an electric connector used for electronic endoscope apparatuses. The electric connector proposed in Japanese Patent No. 2902654 will be described with reference to FIGS. 10 and 11.

First, the concept of the configuration of an electronic endoscope apparatus will be described with reference to FIG. 10. An electronic endoscope apparatus 101 is composed of an electronic endoscope 102, a light source device 103, a video processor 106, and a monitor 107.

The electronic endoscope 102 comprises an elongate, flexible insertion portion 108 for insertion into the body cavity, an operation portion 109 provided on a proximal end of the insertion portion 108 and which is grasped and operated by an operator, and a universal cord 110 as a connection cable which extends from the operation portion 109. The insertion portion 108, the operation portion 109, and the universal cord 110 each contain a light guide 111 and a cable wire 112. One end of the light guide 111 is located at a distal end portion of the insertion portion 108. The other end of the light guide 111 is connected to the light source device 103 by a scope connector 113 provided at a proximal end portion of the universal cord 110. One end of the cable wire 112 is connected to a CCD 115 located at a focal position of an objective lens 114 provided at a distal end of the insertion portion 108 and to a part having a predetermined function, such as a switch described below. The other end of the cable wire 112 is connected to an electric connector 120 provided in the scope connector 113.

Although not shown, the operation portion 109 has a bending operation knob that bendably operates a bending portion provided at the distal end portion of the insertion portion 108, a treatment instrument insertion opening through which a treatment instrument is inserted into a treatment instrument channel in the insertion portion 108, and image processing system switches such as a release switch, a freeze switch, and enhance switch which are used to drivingly control the CCD 115 to manipulate motion pictures, still images, and the like.

Further, the operation portion 109 has an air and water feeding button used to feed air or water to the surface of the objective lens 114, located at the distal end portion of the insertion portion 108, a suction button used to suck feculence or water out of the body cavity, and a water forward feeding button used to feed forward cleaning water used to clean the interior of the body cavity. The image processing system switches, provided in the operation portion 109, are connected to the video processor 106 via the electric connector 120, provided in the scope connector 113 of the universal cord 110.

The air and water feeding pump, which feeds air and water, is provided in the light source device 103. A suction pump for suction and a water forward feeding pump for water forward feeding are separately provided from the light source device 103. These pumps perform air and water feeding, suction, and water forward feeding.

The light source device 103 has a light source lamp 116, a condensing lens 117 that condenses illumination light from the light source lamp 116 to allow the light to enter an input end of the light guide 111, located in the scope connector 113, a lighting and dimming control circuit (not shown) for the light source lamp 116, and the above pumps.

The video processor 106 is a signal processing device (the video processor 106 is hereinafter also referred to as the signal processing device) having a drive circuit 104 that drivingly controls the CCD 115, provided at the distal end of the insertion portion 108 of the electronic endoscope 102, and a signal processing circuit 105 that processes image pickup signals photoelectrically converted by the CCD 115 to generate endoscope video signals. The light source device 103 and the video processor 106 are integrally formed.

The monitor 107 displays endoscope images corresponding to video signals processed by the signal processing circuit 105 in the video processor 106.

The scope connector 113, provided at the proximal end of the universal cord 110, has the electric connector 120 which connects an incident end of the light guide 111 to the light source device 103 and to which the other end of the cable wire 112 in the electronic endoscope 102 is connected, as described above.

The electric connector 120 couples to a connection plug 122 connected to one end of a connection cord 121 comprising a plurality of cables for connection to the video processor 106, serving as an external instrument used in combination with the electronic endoscope 102.

A connection plug 123 similar to the connection plug 122 is provided at the other end of the connection cord 121. The connection plug 123 is coupled to an electric connector 124 provided in the video processor 106. The electric connector 124, provided in the video processor 106, has a configuration substantially similar to that of the electric connector 120, described above.

That is, the electric connector 120 connects to the cable wire 112 comprising a signal wire that connects the CCD 115, provided at the distal end portion of the insertion portion 108, to the video processor 106 in order to transmit and receive a CCD driving control signal, an image pickup signal, a driving power supply, and the like, a signal wire that connects the image processing system switches, provided on the operation portion 109, to the video processor 106, and a signal wire that connects the light source device 103 to the video processor 106 to allow the video processor 106 to perform dimming control on the light source device 103. The electric connector 120 also couples to a connection plug 122 of the connection cord 121 for connection to the video processor 106.

The electric connector 120, provided in the scope connector 113, will be described with reference to FIG. 11. The electric connector 124, provided in the video processor 106, has a configuration substantially similar to that of the electric connector 120 of the scope connector 113 except for the pin configuration, water-tight structure, and the like. Accordingly, the description of the electric connector 124 is omitted.

The electric connector 120 has a cylindrical base 131 including a flange 132 provided around the outer periphery of the base 131 for threadable attachment to the scope connector 113. A cylindrical insulating frame 135 is fitted into the inner periphery of the base 131. A cylindrical guide member 136 is further fitted into the cylindrical insulating frame 135. An engaging projection provided on the inner periphery of a proximal end of a guide member 136 has a cover member 138, and an insulator 139 and a circuit board 141 fixed via a circuit board fastener 142 to a rear surface of the cover member 138 so that the insulator 139 lies on top of the circuit board 141. The guide member 136 is fixedly positioned by a positioning pin 143 engagingly fitted into the base 131 and the cylindrical insulating frame 135. A water-tight packing is interposed between the outer periphery of the circuit board fastener 142 and the inner periphery of the proximal end of the base 131. A cylindrical shield frame 145 is threadably attached to the proximal end of the circuit board fastener 142. A shield member 146 is fixedly attached to the proximal end of the shield frame 145 and has an opening in which the cable wire 112 is inserted. The cable wire 112 is placed in the opening in the shield member 146. The cable wire 112, caught in a cushion member 147, is fixed to a shield member 146 via a cable fastening plate 148 and a screw 149.

Solid wire pins 152 that are a plurality of solid wire terminals, coaxial pins 154 that are a plurality of coaxial terminals, and a post pin 153 penetrate the cover member 138, insulator 139, and circuit board 141, provided inside the proximal end of the guide member 136. Solid wires 155 constituting the cable wire 112 are connected to the solid wire pins 152. A core wire and a shield wire of a coaxial wire 156 constituting the cable wire 112 are connected to the coaxial pins 154. The core wire of the coaxial wire 156 may be connected to one of the solid wire pins 152, while the shield wire may be connected to another solid wire pin 152. The post pin 153 releases static electricity generated when an operator's hand or the like touches any pin.

Moreover, each of the cover member 138, the insulator 139, and the circuit board 141 has a vent 161 that penetrates each of the cover member 138, the insulator 139, and the circuit board 141. A permeable waterproof sheet through which air is passed but not any liquid is attached to the vent 161.

The solid wires 155, connected to the solid wire pins 152, each have a core wire around which an insulating coating is provided. Each of the coaxial wires 156, connected to the coaxial pins 154, comprises a core wire around which an insulating coating is provided and a shield wire which is located around the outer periphery of the insulating coating of the core wire and around which an insulating coating is further provided. Each of the solid wire pins 152 are basically formed only of a pin to which the core wire of the solid wire 155 is connected. Further, each of the coaxial pins 154 comprises a core wire portion and a shield portion which are insulated and isolated from each other and to which the core wire and shield wire, respectively, of the coaxial wire 156 are connected.

The connection plug 122 of the connection cord 121, installed on the electric connector 120 configured as described above, has a pin receiver into which the solid wire pin 152 and the coaxial pin 154 are inserted.

The connection plug 122 of the connection cord 121 connected to the video processor 106 is coupled to the electric connector 120 provided in the scope connector 113 to electrically connect the electronic endoscope 102 to the video processor 106. This allows the supply of driving power to the CCD 115 and the transmission and reception of image pickup signals, various image processing system control signals, and the like. Moreover, the light source device 103 and the video processor 106 are electrically connected together to allow the video processor 106 to perform dimming control and the like.

To remove or replace, for repair, any part of the electronic endoscope 102 using the electric connector 120 configured as described, the following operation is performed. The cable wire 112 is disconnected from the solid wire pins 152 and the coaxial pins 154. Action such as part replacement which is required for the repair is taken. An end of the cable wire 112 is connected back to the solid wire pins 152 and the coaxial pins 154.

For example, to remove, from the electronic endoscope 102 including the CCD 115, an image pickup unit of the electronic endoscope 102 which provides functions for image pickup, the image pickup unit and the cable wire 112 connected to the image pickup unit are removed from the electronic endoscope 102.

Further, to remove any of the electric switches such as the image processing system switches, provided on the operation portion 109, from the electronic endoscope 102 for replacement owing to a defect in the electric switch, that electric switch and the cable wire 112 connected to the electric switch are removed from the electronic endoscope 102.

SUMMARY OF THE INVENTION

An electric connector for an endoscope in accordance with the present invention is provided on a connection cable extending from an operation portion of the endoscope and electrically connects a cable wire extending from the operation portion of the endoscope to an external instrument for use in combination with the endoscope. The electric connector has a circuit board having a connection member that is electrically connected to the external instrument and a connector to which a cable wire connector connected to an end portion of the cable wire is releasably connected.

An endoscope in accordance with the present invention has an insertion portion, an operation portion provided at a proximal end of the insertion portion, and a connection cable extending from the operation portion and including an electric connector for connection to an external instrument. The endoscope comprises a cable wire connector provided at an end portion of the cable wire extending from the operation portion and inserted through the connection cable, and a circuit board having a connection member provided in the electric connector and electrically connected to the external instrument and a connector to which the cable wire connector is releasably connected.

The present invention provides a method for assembling an electric connector which is provided on a connection cable extending from an operation portion of an endoscope and which comprises a circuit board having a first circuit board portion and a second circuit board portion and comprising a flexible circuit board bent so that the first circuit board portion and the second circuit board portion at least partly overlap each other as viewed from a direction orthogonal to a surface of the first circuit board portion, the circuit board having a connection member electrically connected to an external instrument and a connector to which a cable wire connector connected to an end portion of a cable wire extending from the operation portion of the endoscope is releasably connected. The method comprises a first circuit board portion connecting step of inserting the connection member into a hole portion formed in the first circuit board portion to connect the connection member to a land provided around a periphery of the hole portion of the first circuit board portion, a second circuit board portion connecting step of bending the circuit board to insert the connection member projecting from the first circuit board portion into the hole portion formed in the second circuit board portion to connect the connection member to the land provided around the periphery of the hole portion of the second circuit board portion, and a cable wire connector installing step of installing the cable wire connector in the connector of the circuit board.

An endoscope in accordance with the present invention has an insertion portion, an operation portion provided at a proximal end portion of the insertion portion, and a connection cable connected to the operation portion and including an electric connector at a proximal end portion. The endoscope comprises a first cable wire having one end connected to the electric connector and extending into the operation portion, a second cable wire having one end connected to an image pickup portion provided in the insertion portion or an electric switch provided on the operation portion, the second cable wire extending into the operation portion, and a connection member to which the other ends of the first cable wire and the second cable wire together are electrically and releasably connected.

An endoscope in accordance with the present invention has an insertion portion, an operation portion provided at a proximal end portion of the insertion portion, and a connection cable connected to the operation portion and including an electric connector at a proximal end portion. The endoscope has a signal wire for insertion into the endoscope, the signal wire extending from the electric connector toward a distal end and comprising a cable wire and a connector to which an end portion of the cable wire is releasably connected.

BRIEF DESCRIPTION OF THE DRAWINGS

FIG. 3A is a plan view of a front surface of the connector circuit board with the first embodiment;

FIG. 3B is a plan view of a back surface of the connector circuit board with the first embodiment;

BEST MODE FOR CARRYING OUT THE INVENTION

First Embodiment

Figure 1:
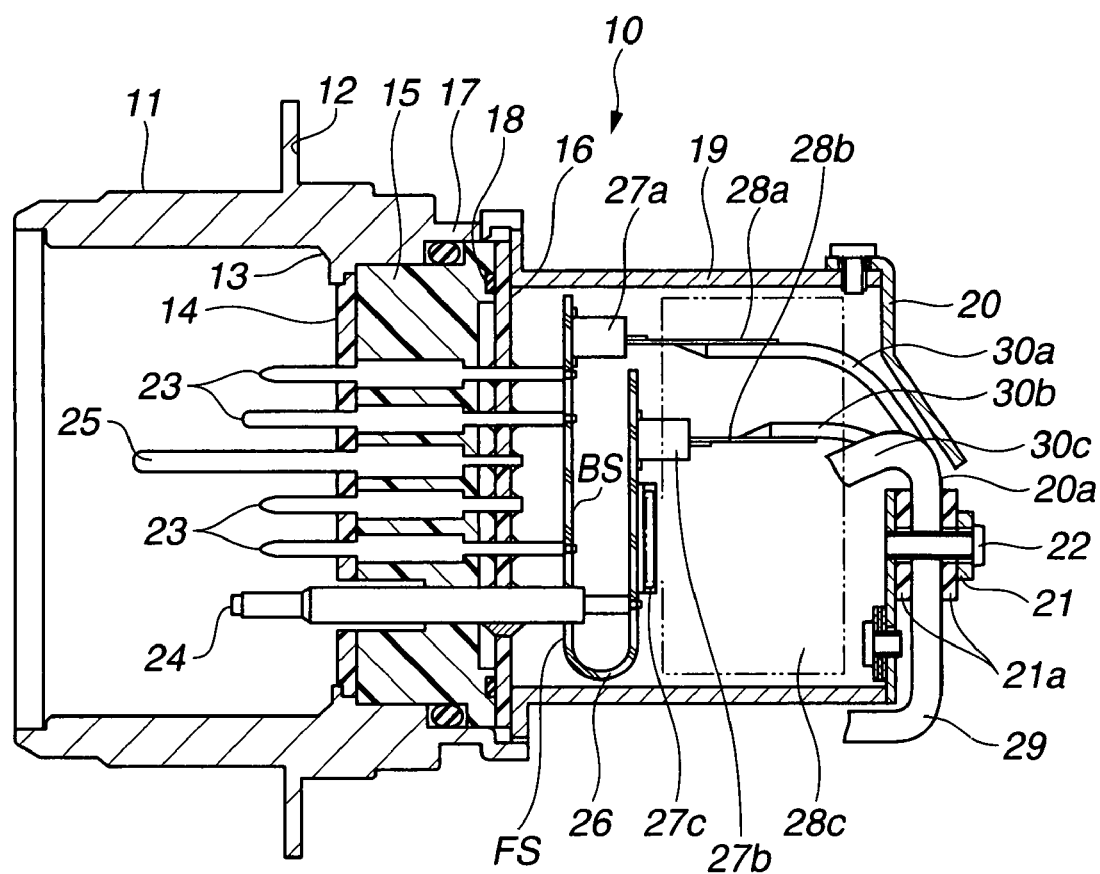
FIG. 1 is a vertical sectional view showing the configuration of an electric connector for an endoscope in accordance with a first embodiment.

An embodiment of the present invention will be described below in detail with reference to the drawings.

An electric connector 10 for an endoscope in accordance with the present embodiment corresponds to the electric connector 120 for the electronic endoscope 102 described above with reference to FIGS. 10 and 11. That is, as described above with reference to FIGS. 10 and 11, the electric connector 10 is provided in the scope connector 113 located at the proximal end of the universal cord 110 extending from the operation portion 109 and serving as a connection cable. The electric connector 10 couples to the connection plug 122 of the connection cord 121 for connection to the video processor 106.

With reference to FIG. 1, description will be given of the configuration of the electric connector for the endoscope in accordance with the present invention. FIG. 1 is a vertical sectional view showing the configuration of the electric connector for the endoscope.

The electric connector 10 for the endoscope in accordance with the present invention (hereinafter simply referred to as the electric connector) has a cylindrically formed base 11 to which the connection plug 122 provided at the end portion of the connection cord 121 described above is coupled. A flange 12 for threadable attachment to the scope connector 113 or the like is provided around the outer periphery of the base 11. An engaging projecting portion 13 is provided at a proximal end of the inner periphery of the base 11. A generally circular cover member 14 abuts against the engaging projecting portion 13. An insulator 15 formed of an insulating member is located on a rear surface of the cover member 14. Moreover, a circuit board 16 is located on a rear surface of the insulator 15. The cover member 14, the insulator 15, and the circuit board 16 are adhesively fixed to one another. The cover member 14, the insulator 15, and the circuit board 16 are penetrated by a solid wire pin serving as a solid wire terminal (hereinafter simply referred to as a solid wire pin) 23, a coaxial pin serving as a coaxial terminal (hereinafter simply referred to as a coaxial pin) 24, and a post pin 25, described later. A packing 17 is interposed between the inner periphery of the base 11 and the outer periphery of the insulator 15. Further, a packing 18 is interposed between the insulator 15 and the vicinity of the outer periphery of the circuit board 16. That is, the cover member 14, the insulator 15, and the circuit board 16 are adhesively fixed to the inner periphery of the base 11 via the packings 17 and 18 in a water-tight manner.

A cylindrical shield frame 19 formed of a conductive shield member is provided on an outer peripheral surface side of a rear surface of the circuit board 16. A distal end of the shield frame 19 is threadably fixed to a proximal end of the base 11 using a screw (not shown) or an external thread formed on the outer periphery of the distal end. Fixing the shield frame 19 to the proximal end of the base 11 electrically contacts the shield frame 19 with a ground potential pattern (not shown) provided on that side of the outer periphery of the circuit board 16 which contacts the shield frame 19; the ground potential pattern is further connected to the base 11 via the shield frame 19. That is, the base 11, the ground potential pattern of the circuit board 16, and the shield frame 19 are electrically connected together.

A shield cap 20 formed of a shield member having an opening 20*a* through which a cable wire 29 is inserted is threadably attached to a proximal end of the shield frame 19. The cable wire 29 is inserted into the opening 20*a* of the shield cap 20. Moreover, the cable wire 29 is fixed to the shield cap 20 by a cable wire fastening plate 21 containing a cushion member 21*a* fixedly attached to the cable wire 29 via a screw 22.

The cable wire 29 is the same as a cable wire 112 described above with reference to FIGS. 10 and 11. That is, one end of the cable wire 29 is electrically connected to an electric part or an electronic part (hereinafter simply referred to as an electric part) which is provided in the insertion portion 108 or the operation portion 109 and which has a predetermined function.

More specifically, the cable wire 29 comprises a scope connector signal wire 30*a*, an operation portion signal wire 30*b*, and an insertion portion signal wire 30*c*. To allow a video processor 106 to control a light source device 103, the scope connector signal wire 30*a* is composed of a signal wire integrated into the scope connector 113 to electrically connect the video processor 106 to the light source device 103. The operation portion signal wire 30*b* is composed of a plurality of signal wires electrically connected to electric parts such as image processing system switches provided on the operation portion 109. Further, the insertion portion signal wire 30*c* is composed of a plurality of signal wires electrically connected to electric parts such as a CCD 115 provided at distal end portion of the insertion portion 108. Here, the insertion portion signal wire 30*c* includes at least one of, for example, a driving signal cable through which signals driving the CCD 115, such as a timing signal outputted by an external apparatus, are transmitted to the CCD 115, a power supply cable through which an external apparatus supplies power to the CCD 115, a CCD driving cable through which required power, a timing signal, and the like are transmitted to the CCD 115, and a video signal cable through which video signals outputted by the CCD 115, such as image signals, are transmitted to an external apparatus.

Further, the scope connector signal wire 30*a*, the operation portion signal wire 30*b*, and the insertion portion signal wire 30*c* each comprise a plurality of solid wires and a coaxial wire. Further, a composite cable includes several solid wires and a coaxial wire or a plurality of coaxial wires. According to the present embodiment, the cable wire 29 is composed of the scope connector signal wire 30*a*, the operation portion signal wire 30*b*, and the insertion portion signal wire 30*c*. Alternatively, the cable wire 29 may be composed of one or two of the scope connector signal wire 30*a*, the operation portion signal wire 30*b*, and the insertion portion signal wire 30*c*.

The operation portion signal wire 30*b* may be connected to electric parts provided in the operation portion other than the image processing system switches. Further, the insertion portion signal wire 30*c* may be electrically connected to electric parts such as a light emitting device (for example, a LED) provided at the distal end of the insertion portion 108 to illuminate a subject.

Cable wire connectors 28*a*, 28*b*, and 28*c* (alternate long and two short dashes line in the figure) formed on a flexible circuit board in accordance with the present invention described below are connected to the distal ends of the scope connector signal wire 30*a*, operation portion signal wire 30*b*, and insertion portion signal wire 30*c*, which corresponds to that end portion of the cable wire 29.

A plurality of solid wire pins 23, a plurality of coaxial pins 24, and a single post pin 25 are disposed around the inner periphery of the base 11 and serve as a connection member connecting to a connection plug 122 of a connection cord 121 from a signal processing device (in the present embodiment, the video processor 106) serving as an external instrument. The solid wire pins 23, the coaxial pins 24, and the post pin 25 penetrate the cover member 14 and the insulator 15 and are fixed to the circuit board 16. With the connection plug 122 coupled to the electric connector 10, the solid wire pins 23, coaxial pins 24, and post pin 25 projecting from a distal end surface of the cover member 14 are inserted into a pin receiver provided in the connection plug 122, coupled to the inner periphery of the base 11. The post pin 25 projects further toward the side to which the connection plug 122 of the connection cord 121 is coupled, than the solid wire pins 23 and the coaxial pins 24. Thus, if the operator's hand touches the interior of the base 11, the operator's hand touches the post pin 25 before touching the solid wire pins 23 and the coaxial pins 24. This makes it possible to release static electricity charged on the operator.

The solid wire pins 23, the coaxial pins 24, and the post pin 25 are adhesively fixed to the insulator 15. The proximal ends of the solid wire pins 23, the coaxial pins 24, and the post pin 25 are inserted into respective through holes formed in the circuit board 16 and soldered to lands provided around the periphery of the through-holes.

The solid wire pins 23 and the coaxial pins 24 are soldered to the circuit board 16 and extend proximally from the circuit board 16. Moreover, the solid wire pins 23 and the coaxial pins 24 are inserted into the respective through holes formed in a connector circuit board 26 and soldered to the lands provided around the periphery of the through-holes.

Although the configuration of the connector circuit board 26 will be described below in detail, the connector circuit board 26 has the through-holes as hole portions into which the solid wire pins 23 and the coaxial pins 24 are inserted, the lands for soldering which are arranged around the respective through-holes, and connectors 27a, 27b, 27c in which cable wire connectors 28a, 28b, 28c provided at distal ends of the scope connector signal wire 30a, operation portion signal wire 30b, and insertion portion signal wire 30c of the cable wire 29 are installed. Further, the connector circuit board 26 has the lands to which the solid wire pins 23 and the coaxial pins 24 are soldered and connection patterns that electrically connect the connectors 27a, 27b, 27c together. In the present embodiment, the cable wire connectors 28a, 28b, and 28c are collectively called a cable wire connector 28. The connectors 27a, 27b, and 27c are collectively called a connector 27.

That is, the electric connector 10 in accordance with the present embodiment mainly comprises the base 11 to which the connection plug 122 is coupled, the plurality of solid wire pins 23 and coaxial pins 24 provided through the cover member 14, insulator 15, and circuit board 16 in the base 11, the connector circuit board 26 having the through-holes through which the solid wire pins 23 and the coaxial pins 24 are inserted, the lands provided around the periphery of the respective through-holes, and the connectors 27a, 27b, 27c, the cable connectors 28a, 28b, 28c that connect the cable wire 29 to the connector 27 of the connector circuit board 26, the shield frame 19 that covers the connector circuit board 26 and the cable wire connector 28, and the shield cover 20 provided on the shield frame 19.

The configuration of the base 11, cover member 14, insulator 15, circuit board 16, shield frame 19, and shield cover 20, and the like of the electric connector 10 may be the shape and configuration described above with reference to FIG. 11.

Figure 2:
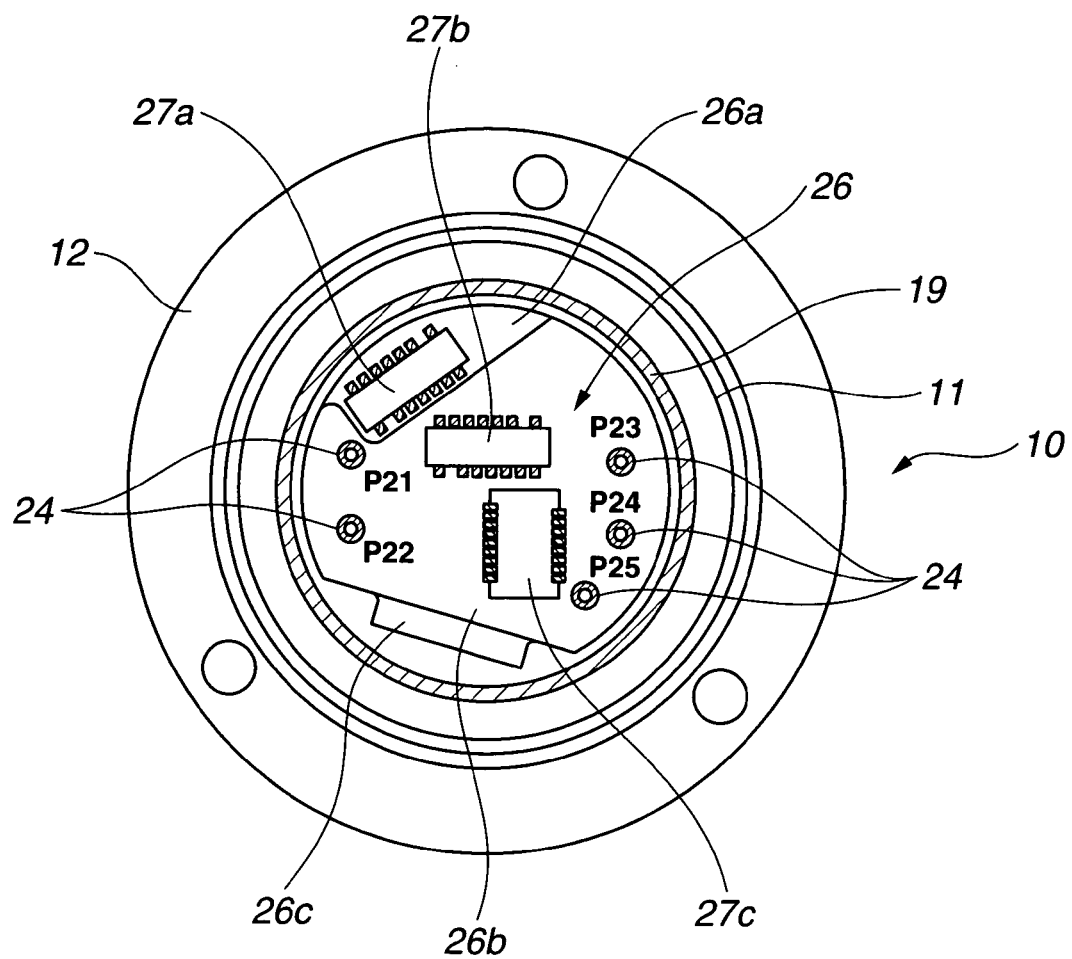
FIG. 2 is a plan view showing that a connector circuit board is mounted in a shield frame of the electric connector in accordance with the first embodiment.

Now, with reference to FIGS. 1, 2, 3A and 3B, description will be given of the connector circuit board 26, provided in the electric connector 10 in accordance with the present invention. FIG. 2 is a plan view showing that the connector circuit board is mounted in the shield frame of the electric connector. FIG. 3A is a plan view of the front surface of the connector circuit board. FIG. 3B is a plan view of the back surface of the connector circuit board.

As shown in FIGS. 1 and 2, the connector circuit board 26 soldered to the solid wire pins 23 and the coaxial pins 24 is provided in the shield frame 19 of the electric connector 10. The connector circuit board 26 is formed of a single flexible circuit board and mainly comprises a generally circular first circuit board portion 26a to which shield portions of the solid wire pins 23 (not shown) and the coaxial pins 24 are connected, a generally circular second circuit board portion 26b connecting to the connector 27 in which the cable wire connector 28, provided at the distal ends of the signal wires 30a to 30c of the cable wire 29, is installed and to core wire portions of the coaxial pins 24, and a bendable portion 26c having a connection pattern (not shown) that electrically connects the first circuit board portion 26a to the second circuit board portion 26b, the bendable portion 26c being bendable into a general U shape such that the first circuit board portion 26a lies opposite the second circuit board portion 26b. The connector circuit board 26 is disposed in the shield frame 19 by being bent into a U shape at the bendable portion 26c so that a front surface FS is located outside, whereas a back surface BS is located inside. The flexible circuit board is also called a flexible printed circuit board (hereinafter also referred to as an FPC) and constructed by providing a conductor circuit on a film comprising a material such as polyimide which offers heat resistance and an insulating property.

The configuration of the connector circuit board 26 will be described with reference to FIG. 3A and FIG. 3B. The first circuit board portion 26a of the back surface of the connector circuit board 26 (see FIG. 3B) has solid wire pin lands 52 comprising through-holes 52a as hole portions into which the plurality of solid wire pins 23 are inserted and lands 52b provided around the periphery of the respective through-holes 52a. Further, the first circuit board portion 26a of the back surface of the connector circuit board 26 has coaxial shield pin lands 53 comprising through-holes 53a as hole portions into which the shield portions of the plurality of coaxial pins 24 are inserted and lands 53b each provided around that part of the periphery of the corresponding through-hole 53a which is closer to the outer edge of the first circuit board portion 26a. Moreover, the first circuit board portion 26a of the back surface of the connector circuit board 26 is equipped with the connector 27a in which the cable wire connector 28a of the scope connector signal wire 30a is installed.

The connector 27a, in which the cable wire connector 28a is installed, is mounted on the outer periphery of the first circuit board portion 26a. Further, the solid wire pin lands 52 are mostly provided closer to the center of the first circuit board portion 26a as shown by P1 to P19 in the figure. The coaxial shield pin lands 53 are provided closer to the outer edge of the first circuit board portion 26a than the solid wire pin lands 52, provided closer to the center, as shown by P21 to P25 in the figure.

The second circuit board portion 26b of the back surface (see FIG. 3B) of the connector circuit board 26 has coaxial core wire pin lands 55 (P31 to P35 in the figure) comprising through-holes 55a formed opposite the coaxial shield pin lands 53 (P21 to P25 in the figure) of the first circuit board portion 26a as hole portions into which the core wire portions of the coaxial pins 24 are inserted when the connector circuit board 26 is bent at the bendable portion 26c so that the back surface of the second circuit board portion 26b lies opposite the back surface of the first circuit board portion 26a, the coaxial core wire pin lands 55 further comprising lands 55b provided around the periphery of the respective through-holes 55a. Further, a shield film 54 is formed over the entire area of the second circuit board portion 26b of the back surface of the connector circuit board 26 other than the areas in which the coaxial core wire pin lands 55 are formed. Shield film 54 is mainly intended to electromagnetically block the first circuit board portion 26a from the second circuit board portion 26b. The shield film 54 extends from the bendable portion 26c to a part of the first circuit board portion 26a and is electrically connected to a ground potential pattern (not shown).

On the other hand, the first circuit board portion 26a of the front surface (see FIG. 3A) of the connector circuit board 26 has solid wire pin lands 52' comprising holes 52'a that are in communication with the through-holes 52a of the corresponding solid wire pin lands 52 (P1 to P19) on the back surface and lands 52'b provided around the periphery of the respective holes 52'a. Further, the first circuit board portion 26a of the front surface of the connector circuit board 26 has holes 53'a that are in communication with the through-holes 53a of the corresponding coaxial shield pin lands 53 (P21 to P25) on the back surface. The second circuit board portion 26b of the front surface of the connector circuit board 26 has holes 55'a that are in communication with the through-holes 55a of the corresponding coaxial core wire pin lands 55 (P31 to P35) on the back surface and coaxial core wire pin lands 55' (P31 to P35) comprising lands 55'b provided around the periphery of the respective holes 55'a.

Moreover, a central portion of the second circuit board portion 26b of the front surface (see FIG. 3A) of the connector circuit board 26 is equipped with the connector 27b in which the cable wire connector 28b connected to the operation portion signal wire 30b of the cable wire 29 is installed and the connector 27c in which the cable wire connector 28c connected to the insertion portion signal wire 30c is installed.

The second circuit board portion 26b has a notch formed in a portion thereof such that when the connector circuit board 26 is bent into a U shape so that the back surface of the board 26 lies inside, the notch overlaps the connector 27a, provided in the first circuit board portion 26a. The notch in the second circuit board portion 26b exposes the connector 27a, facilitating the installation of the cable wire connector 28a in the connector 27a, mounted on the first circuit board portion 26a.

That is, when the connector circuit board 26, formed of a flexible circuit board, is bent at the bendable portion 26c so that the first circuit board portion 26a overlaps the second circuit board portion 26c, the connection members such as the solid wire pins 23, the coaxial pins 24 which are mostly connected to the external instrument are connected to one surface side comprising the front surface of the first circuit board portion 26a and the back surface of the second circuit board portion 26b. The other surface side comprising the back surface of the first circuit board portion 26a and the front surface of the second circuit board portion 26b is equipped with the connectors 27a, 27b, 27c, in which the cable wire connectors 28a, 28b, 28c connected to the cable wire 29 integrated into the universal cord 110 of the electronic endoscope are installed.

The connectors 27a to 27c, provided on the first circuit board portion 26a of the back surface (see FIG. 3B) of the connector circuit board 26 and on the second circuit board portion 26b of the front surface (see FIG. 3A) are connected, via connection patterns (not shown), to some of the solid wire pin lands 52 (P1 to P19), coaxial shield pin lands 53 (P21 to 25), and coaxial core wire pin lands 55 (P31 to P35), provided on the connector circuit board 26.

According to the present embodiment, the following are only illustrative: the numbers of the solid wire pin lands 52 (P1 to P19), coaxial shield pin lands 53 (P21 to P25), and coaxial core wire pin lands 55 (P31 to P35), provided on the connector circuit board 26, as well as the number of the connectors 27a to 27c, provided in the connector circuit board 26. These numbers may be arbitrarily varied depending on the type, thickness, and number of the signal wires 30a to 30c, contained in the cable 29, the number of poles in the connector 27, and the like. Further, the following are only illustrative and may be varied: the number and positions of the connectors 27a to 27c, provided in the first circuit board portion 26a and second circuit board portion 26b of the connector circuit board 26, and the combination of the scope connector signal wire 30a, operation portion signal wire 30b, and insertion portion signal wire 30c for connection to the connectors 27a to 27c. For example, depending on the type, and number of the signal wires 30a to 30c of the scope connector, the operation portion and the insertion portion, contained in the cable 29, the number of poles in the connector 27, and the like, only the two connectors 27b, 27c may be provided in the second circuit board portion 26b without providing the connector 27a on the first circuit board portion 26a, or the three connectors 27a to 27c may be provided in the second circuit board portion 26b. If only the two connectors 27b, 27c are provided in the second circuit board portion 26b without providing the connector 27a on the first circuit board portion 26a or the three connectors 27a to 27c are provided in the second circuit board portion 26b, no notch needs to be formed in the second circuit board portion 26b.

Figure 4:
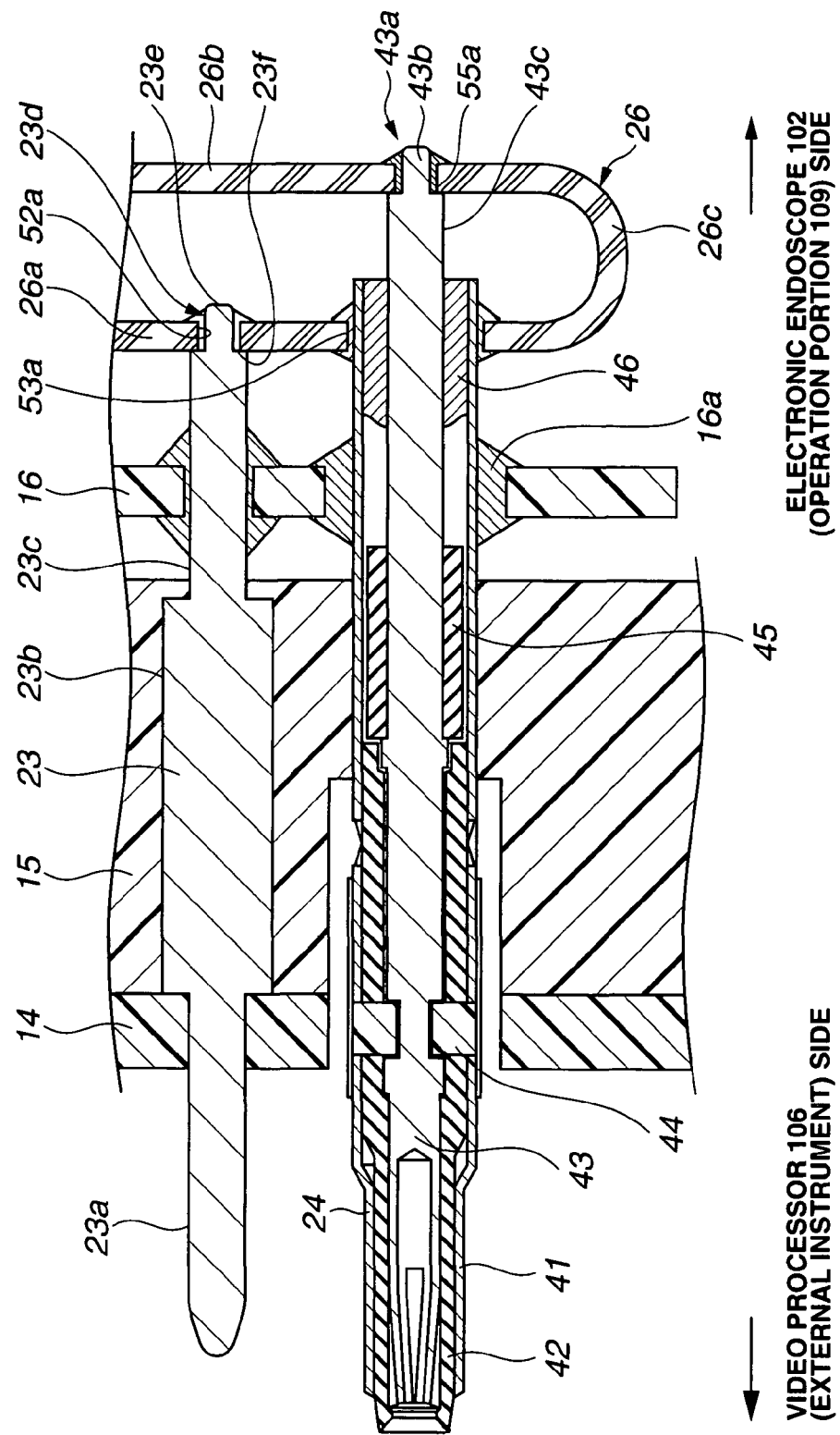
FIG. 4 is a vertical sectional view showing the configuration of a solid wire pin and a coaxial pin which are used in the electric connector in accordance with the first embodiment.

Now, with reference to FIG. 4, description will be given of the solid wire pins 23 and coaxial pins 24, used in the electric connector 10 in accordance with the present invention. FIG. 4 is a sectional view showing the relationship between the configuration of the solid wire pins and coaxial pins, used in the electric connector, and the connector circuit board.

Each of the solid wire pins 23 is a terminal comprising a distal end portion 23a, an intermediate portion 23b, a circuit board fixing portion 23c, and a terminal portion 23d arranged in this order from the video processor 106 (external instrument) side shown in the figure. The distal end portion 23a extends through the cover member 14 toward the video processor 106. Coupling the connection plug 122 to the electric connector 10 causes the distal end portion 23a to be installed in a solid wire receiving plug in the connection plug 122. The intermediate portion 23b is inserted through the insulator 15 and is adhesively fixed in a water-tight manner. The circuit board fixing portion 23c is soldered to the circuit board 16. The circuit board 16 and the solid wire pin 23 are soldered to each other at the circuit board fixing portion 23c to hold the positional relationship between the insulator 15 and the circuit board 16 and to electrically connect the solid wire pin 23 to the connection pattern provided on the circuit board 16. The terminal portion 23d is inserted into the through-hole 52a of the corresponding solid wire pin land 52 on the first circuit board portion 26a of the connector circuit board 26 and then fixedly soldered to the corresponding land 52b.

The terminal portion 23d (shown as the electronic endoscope 102 (operation portion 109) side in the figure) of the solid wire pin 23 has a projecting portion 23e with an outer diameter appropriate for insertion into the through-hole 52a of the corresponding solid wire pin land 52 on the first circuit board portion 26a of the connector circuit board 26, and a step portion 23f having an outer diameter larger than the inner diameter of the through-hole 52a and abutting against the land 52b, provided around the periphery of the corresponding through-hole 52a. That is, the projecting portion 23e of the terminal portion 23d is inserted into the through-hole 52a in the solid wire pin land 52 on the first circuit board portion 26a. The step portion 23f abuts against the land 52b around the periphery of the through-hole 52a.

Each of the coaxial pins 24 comprises a shield portion 41 that is a cylindrical external conductor serving as a second conductor, a cylindrical insulator 42 provided around the inner periphery of the shield portion 41, and a core wire portion 43 provided around the inner periphery of insulator 42 and which is a cylindrical internal conductor serving as a first conductor.

When the connection plug 122 is coupled to the electric connector 10, the shield wire portion of the coaxial receiving plug, provided in the connection plug 122, described above, is installed around the outer periphery of the distal end of the shield portion 41 (shown as the video processor 106 (external instrument) side in the figure). Further, at this time, the core wire portion of the coaxial receiving plug, provided in the connection plug 122, is inserted into a core wire insertion portion formed at the distal end of the core wire portion 43 in an axial direction.

The shield portion 41, the insulator 42, and the core wire portion 43 are fixedly tightened from the outer periphery thereof by a support member 44 via an opening formed in the shield portion 41 so as not to be misaligned with respect to one another. The insulator 42, provided between the shield portion 41 and the core wire portion 43, extends from the distal end side to substantially central portions of the shield portion 41 and core wire portion 43. A support sleeve 45 is provided at a proximal end of the insulator 42 around the outer periphery of the core wire portion 43 in order to maintain an appropriate distance between the shield portion 41 and the core wire portion 43. An elastic filler 46 is filled between the shield portion 41 and the core wire portion 43 at a proximal end of the support sleeve 45. The elastic filler 46 closes the area between the shield portion 41 and the core wire portion 43 so as to prevent water or the like from entering the interior of the electric connector 10.

The shield portion 41, insulator 42, and core wire portion 43 are not completely fixed by the support member 44 but so as to prevent the insulator 42 and the core wire portion 43 from slipping off from the shield portion 41 and to allow the core wire portion 43 to swing slightly with respect to the shield portion 41. Moreover, the elastic filler 46 is filled so as not to completely fix the shield portion 41 but to allow the core wire portion 43 to swing.

The core wire portion 43 is fixed to the shield portion 41 so as to be able to swing with respect to the shield portion 41 because when the electric connector 10 is coupled to the connection plug 122, the completely fixed core wire portion 43 may cause the bending or breaking of the core wire portion of the coaxial receiving plug of the connection plug 122 for insertion into the distal end of the core wire portion 43. By allowing the core wire portion 43 to swing to absorb a force involved in the insertion of the core wire portion of the coaxial receiving plug of the connection plug 122, it is possible to avoid the bending or breaking of the core wire portion of the coaxial receiving plug.

The thus configured coaxial pin 24 is inserted through through-holes formed in the cover member 14 and the insulator 15 and further through a through-hole formed in the circuit board 16. The coaxial pin 24 is then soldered, with a solder 16a, to the land provided around the periphery of the through-hole in the circuit board 16. The coaxial pin 24 placed in the through-holes in the cover member 14 and the insulator 15 is adhesively fixed to the cover member 14 and the insulator 15 in order to keep the interior of the electric connector 10 water-tight.

Moreover, the shield portion 41 of the coaxial pin 24 is soldered to the land 53b with the terminal of the shield portion 41 (shown as the electronic endoscope 102 (operation portion 109) side in the figure) placed in the through-hole 53a of the corresponding coaxial shield pin land 53 on the first circuit board portion 26a of the connector circuit board 26.

A terminal portion 43a (shown as the electronic endoscope 102 (operation portion 109) side in the figure) of the core wire portion 43 of the coaxial pin 24 has a projecting portion 43b with an outer diameter appropriate for insertion into the through-hole 55a of the corresponding coaxial core wire pin land 55 on the second circuit board portion 26b of the connector circuit board 26, and a step portion 43c having an outer diameter larger than the inner diameter of the through-hole 55a and abutting against the land 55b, provided around the periphery of the corresponding through-hole 55a. That is, the projecting portion 43b of the terminal portion 43a of the core wire portion 43 is inserted into the through-hole 55a of the corresponding coaxial core wire pin land 55 on the second circuit board portion 26b. The step portion 43c then abutted against the land 55b, provided around the periphery of the corresponding through-hole 55a. The terminal portion 43a of the core wire portion 43 of the coaxial pin 24 is soldered to the second circuit board portion 26b with the projecting portion 43b placed in the through-hole 55a and the step portion 43c abutted against the land 55b.

Figure 5:
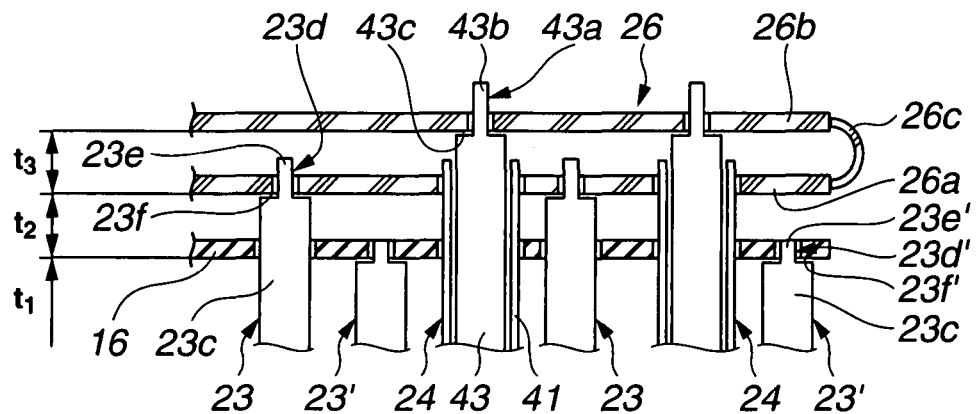
FIG. 5 is a sectional view illustrating the positional relationship between the solid wire pins and the coaxial pins and the connector circuit board, which are used in the electric connector in accordance with the first embodiment.

With reference to FIG. 5, description will be given of the connections between the connector circuit board 26 and the solid wire pins 23 and the coaxial pins 24 which are configured as described above inside the electric connector 10. The solid wire pins 23 and the coaxial pins 24 are electrically connected to the circuit board 16 and to the connector circuit board 26 by soldering to mechanically fix together the circuit board 16 and the first circuit board portion 26a and second circuit board portion 26b of the connector circuit board 26 and to maintain appropriate distances between the circuit board 16 and each of the first circuit board portion 26a and second circuit board portion 26b.

As described above with reference to FIG. 4, the circuit board fixing portion 23c of each solid wire pin 23 extends to a position where the circuit board fixing portion 23c is fixedly soldered to the first circuit board portion 26a of the connector circuit board 26. However, as shown in FIG. 5, the electric connector 10 internally has a solid wire pin 23' having the same shape and configuration as those of the solid wire pin 23 and having a shorter length from the distal end portion 23a to the step portion 23f of the terminal portion 23d than the solid wire pin 23. The shorter solid wire pin 23' is mainly intended for electric connection to the circuit board 16 and for the maintenance of the position of the circuit board 16.

The plurality of shorter solid wire pins 23' are provided in the cover member 14 and the insulator 15 so that step portions 23f of terminal portions 23d' are positioned at least at the same height t1 from the insulator 15. Each of the solid wire pins 23' is soldered to the corresponding land on the circuit board 16 with the projecting portion 23e' of the terminal portion 23d' placed in the through-hole formed in the circuit board 16 and with the step portion 23f abutted against the periphery of the through-hole in the circuit board 16. This maintains a given distance t1 between the circuit board 16 and the insulator 15 and electrically connects the circuit board 16 and the shorter solid wire pin 23' together according to the present embodiment. The circuit board 16 has a connection pattern for connection to electronic parts mounted on the circuit board 16 and a ground potential pattern. The plurality of shorter solid wire pins 23' are electrically connected to the connection pattern or the ground potential pattern via the soldered land.

On the other hand, the plurality of solid wire pins 23 are provided in the cover member 14 and the insulator 15 so that the step portions 23f of terminal portions 23d of the solid wire pins 23 are positioned at least at the same height t2 from the circuit board 16. Each of the solid wire pins 23 is soldered to the first circuit board portion 26a with the projecting portion 23e of the terminal portion 23d placed in the through-hole 52a of the corresponding solid wire pin land 52 on the first circuit board portion 26a of the connector circuit board 26 and with the step portion 23f abutted against the land 52b, provided around the periphery of the corresponding through-hole 52a. This maintains a given distance t2 between the circuit board 16 and the first circuit board portion 26a of the connector circuit board 26 and electrically connects the circuit board 16 and the first circuit board portion 26a of the connector circuit board 26.

The plurality of coaxial pins 24 are provided in the cover member 14 and the insulator 15 so that the step portions 43c of terminal portions 43a of the core wire portion 43 of the coaxial pins 24 are positioned at least at the same height t3 from the first circuit board portion 26a of the circuit board 26.

Each of the coaxial pins 24 is soldered to the second circuit board portion 26b with the projecting portion 43b of the terminal portion 43a of the core wire portion 43 placed in the through-hole 55a of the corresponding coaxial core wire pin land 55 on the second circuit board portion 26b of the connector circuit board 26 and with the step portion 43c abutted against the land 55b, provided around the periphery of the corresponding through-hole 55a. This maintains a given distance t3 between the first circuit board portion 26a and second circuit board portion 26b of the connector circuit board 26 and electrically connects the first circuit board portion 26a to the second circuit board portion 26b.

The first circuit board portion 26a of the connector circuit board 26 is soldered to the terminal portions 23d of the solid wire pins 23 and to the terminal portions of the shield portions 41 of the coaxial pins 24 with the solid wire pins 23 and the coaxial pins 24 inserted through the through-holes 52a and 53a, respectively, in the first circuit board portion 26a.

Thus, the step portions formed in the solid wire pins 23 and 23' and the coaxial pins 24 provided in the cover member 14 and insulator 15 in the base 11, are provided at the predetermined intervals. This makes it possible to mechanically maintain appropriate distances between the circuit board 16 and each of the first circuit board portion 26a and second circuit board portion 26b of the connector circuit board 26 and to electrically connect the circuit board 16, the first circuit board portion 26a, and second circuit board portion 26b together. In general, dedicated holding members are used to fix the circuit boards together and to maintain appropriate distances between the circuit boards. However, the present invention makes it possible to fix the circuit board 16 and the connector circuit board 26 together, while maintaining the appropriate distance between the circuit boards, without using any dedicated holding member.

When the connector circuit board 26 is fixedly soldered to the inside of the base 11 of the electric connector 10, with the base 11 placed so that the solid wire pins 23, the coaxial pins 24, and the post pin 25 in the base 11 lie perpendicular to a workbench, the pin lands 52, 53, and 55 may be inserted around the perpendicularly extending solid wire pins 23 and coaxial pins 24 so that the first circuit board portion 26a and second circuit board portion 26b lie level to the solid wire pins 23 and the coaxial pins 24. This enables the two-dimensional operation of soldering the solid wire pins 23 and the coaxial pins 24 to the connector circuit board 26, increasing the efficiency of the soldering operation.

Further, only the terminal portions 43a of the core wire portions 43 of the coaxial pins 24 are connectively soldered to the second circuit board portion 26b of the connector circuit board 26. Consequently, the second circuit board portion 26b of the connector circuit board 26 swings in conjunction with swinging of the core wire portions 24. This prevents swinging of the core wire positions 43 from being hindered by the connection between the core wire portions 43 and the second circuit board portion 26b. Thus, when the electric connector 10 is coupled to the connection plug 122, it is possible to avoid the bending or breaking of the core wire portion of the coaxial receiving plug by allowing the core wire portions 43 to swing to absorb a force involved in the insertion of the core wire portion of the coaxial receiving plug of the connection plug 122.

Moreover, the solid wire pin lands 52, coaxial shield pin lands 53, and coaxial core wire pin lands 55, provided on the first circuit board portion 26a and second circuit board portion 26b of the connector circuit board 26, are arranged substantially symmetrically with respect to the center of the first and second circuit board portions 26a, 26b. Thus, the solid wire pins 23 and the coaxial pins 24 are fixedly soldered to the pin lands 52, 53, 55 for the solid wires, the coaxial shields, and the coaxial core wires to enable the first circuit board portion 26a and the second circuit board portion 26b to be fixed together with the first and second circuit board portions 26a and 26b kept planar. This makes it possible to stabilize the maintenance of the appropriate distance between the first circuit board portion 26a and the second circuit board portion 26b and the planar fixation of the first and second circuit board portions 26a and 26b.

Moreover, the second circuit board portion 26b has the notch so as to, when the connector circuit board 26 is bent into a U shape at the bendable portion 26c, prevent the possible interference such as the possible contact between the second circuit board portion 26b and the connector 27a, which is a part mounted on an inner surface of the U shape of the first circuit board portion 26a. This allows the second circuit board portion 26b to be shifted closer to the first circuit board portion 26a to the same position as that of the connector 27a or a position lower than the connector 27a. This makes it possible to reduce that part of the relatively small space in the shield frame 19 of the electric connector 10 which is occupied by the connector circuit board 26.

If interference such as contact occurs between any part mounted on the first circuit board portion 26a of the connector circuit board 26 and the second circuit board portion 26b, the distance between the first circuit board portion 26a and the second circuit board portion 26b may be increased using the coaxial pins 24 having a varying dimension between the terminal of the shield portion 41 and the terminal portion 43a of the core wire portion 43 of the coaxial pin 24 depending on the height of the part mounted on the second circuit board portion 26b. Alternatively, the overall height of the connector circuit board 26 may be reduced by installing the parts otherwise mounted on the connector circuit board 26 only on the second circuit board portion 26b to decrease the distance between the first circuit board portion 26a and the second circuit board portion 26b.

Figure 6:
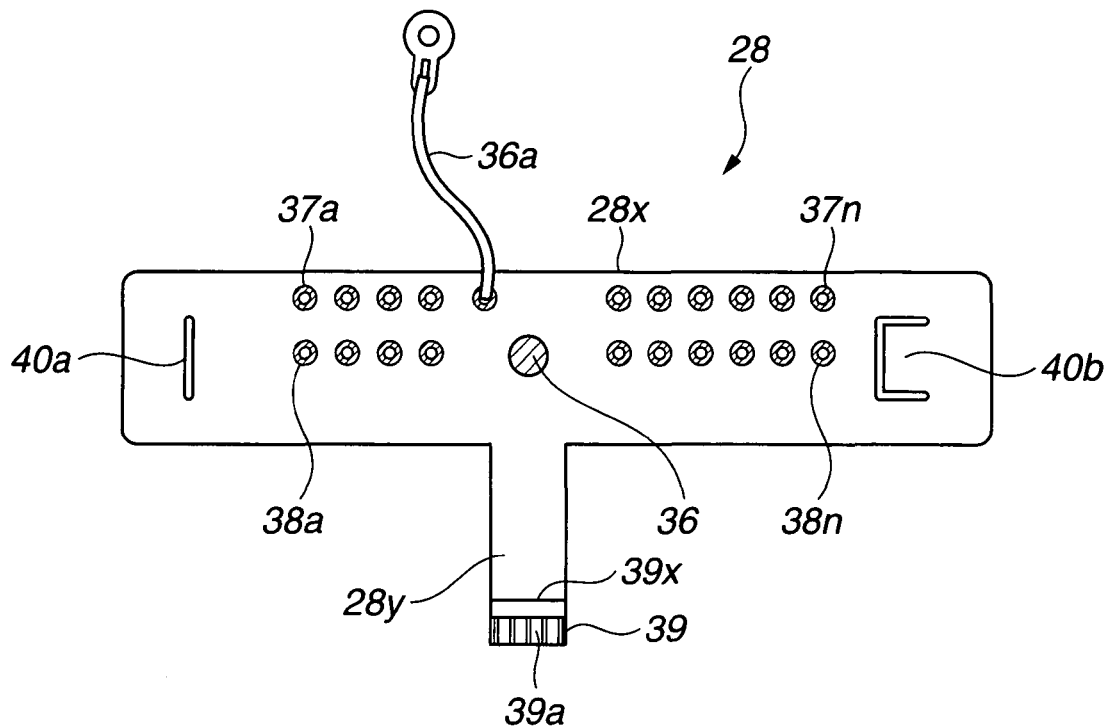
FIG. 6 is a plan view showing the configuration of a cable wire connector used in the electric connector in accordance with the first embodiment.
Figure 7:
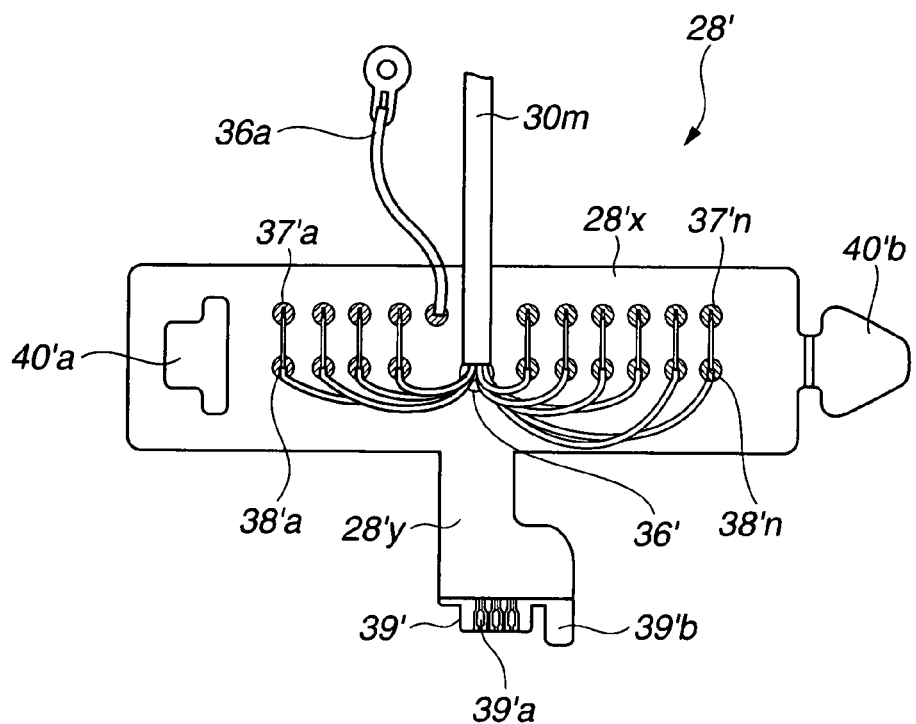
FIG. 7 is a plan view showing the configuration of a first variation of the cable wire connector used in the electric connector in accordance with the first embodiment.
Figure 8:
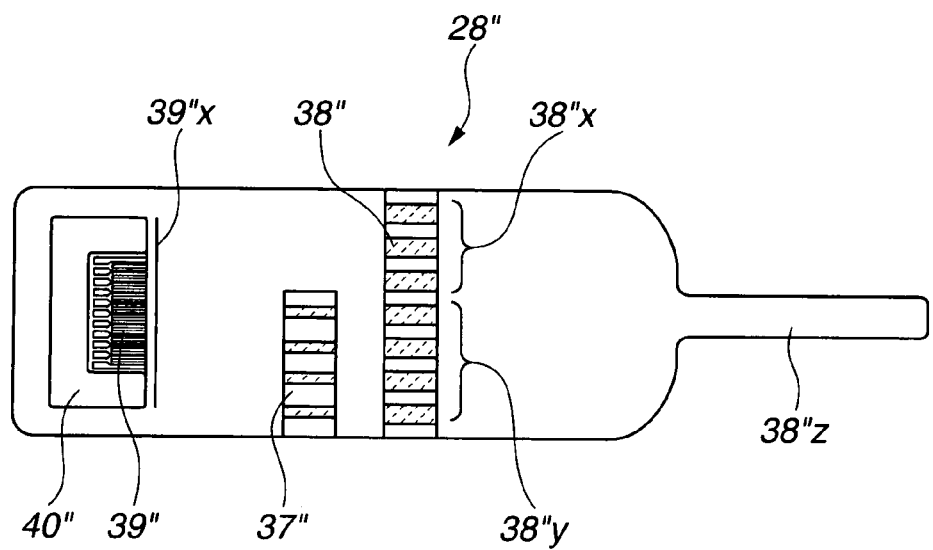
FIG. 8 is a plan view showing the configuration of a second variation of the cable wire connector used in the electric connector in accordance with the first embodiment.
Figure 9:
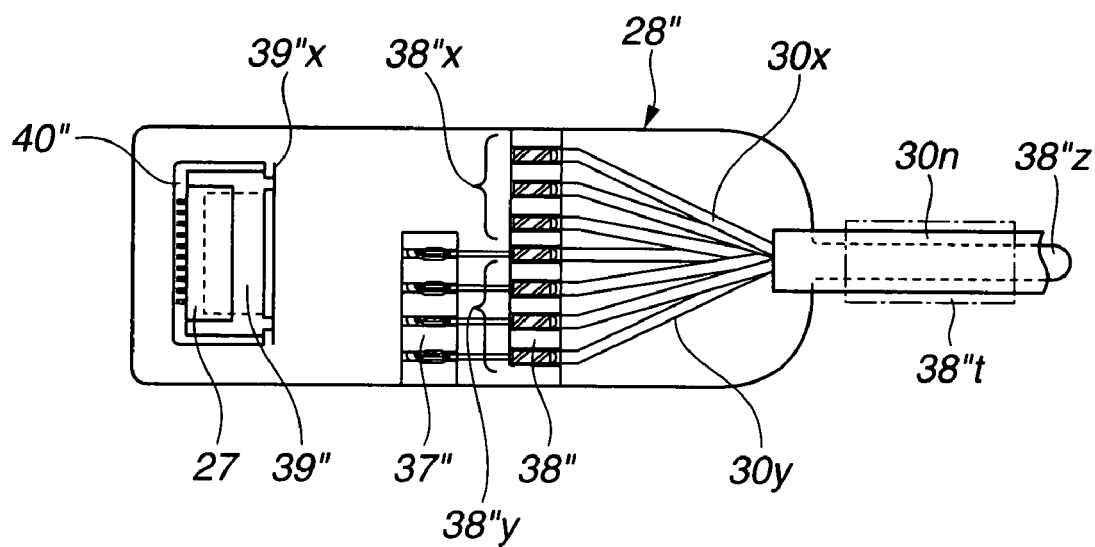
FIG. 9 is a plan view illustrating how signal wires are connected to and installed on the connector in accordance with the second variation of the cable wire connector used in the electric connector in accordance with the first embodiment.

Now, with reference to FIGS. 6 to 9, description will be given of the cable wire connectors 28a, 28b, and 28c, connected to the distal ends of the scope connector signal wire 30a, operation portion signal wire 30b, and insertion portion signal wire 30c, which are arranged at an end portion of the cable wire 29. In the present embodiment, the cable wire connectors 28a, 28b, and 28c are collectively called a cable wire connector 28. FIG. 6 is a plan view showing the cable wire connector provided at the distal end of the cable wire used in the electric connector. FIG. 7 is a plan view of a first variation of the cable wire connector. FIG. 8 is a plan view of a second variation of the cable wire connector. FIG. 9 is a plan view illustrating the connection of signal wires and the installation of the signal wires in the connector in accordance with the second variation of the cable wire connector.

First, with reference to FIG. 6, description will be given of the cable wire connector 28, connected to the distal end of the cable wire 29.

The cable wire connector 28 generally has a T shape comprising a cable wire connection portion 28x formed of a flexible circuit board and shaped like a rectangle, the cable wire connection portion 28x being located in the horizontal direction of the sheet of the drawing, and a connection terminal portion 28y extending in the vertical direction of the sheet of the drawing from a substantially central portion of the cable wire connection portion 28x.

The cable wire connection portion 28x two-dimensionally has connection lands 37a to 37n and 38a to 38n arranged in two longitudinal lines at substantially equal intervals and to which a plurality of electric wires are connected. In the present embodiment, the connection lands 37a to 37n and 38a to 38n are collectively called connection lands 37 and 38. The solid wires and coaxial wires of each of the scope connector signal wire 30a, operation portion signal wire 30b, insertion portion signal wire 30c, and the like of the cable wire 29 are two-dimensionally soldered to the connection lands 37 and 38. For example, each of the solid wires is soldered to one of the connection lands 37. The core wire of each of the coaxial wires is soldered to one of the connection lands 37. The shield wire of the coaxial wire is soldered to one of the connection lands 38.

Each of the connection lands 37, 38 may have a through-hole serving as a hole portion for indexation and into which an electric wire is inserted, and a soldering land provided around the periphery of the through-hole, or may have only a land to which an electric wire is soldered, with no through-hole formed therein. The intervals of the individual connection lands 37, 38 provided on the cable wire connection portion 28x is set to facilitate soldering connections in accordance with the types, thicknesses, or the like of the solid wires and the coaxial wires to be connected. Thus, the present embodiment facilitates the operation of connectively soldering the cable wire 29 to the cable wire connector 28 because the operation can be performed with the cable wire 29 two-dimensionally placed with respect to the cable wire connector 28.

A generally I-shaped kerf 40a is formed at one end portion of the cable wire connection portion 28x in a longitudinal direction thereof by making a slit parallel to the end portion in the cable wire connection portion 28x. A generally C-shaped kerf 40b is formed at the other end portion of the cable wire connection portion 28x also by cutting into the cable wire connection portion 28x.

A grounding land 36 is provided in a substantially central portion of the cable wire connection portion 28x so that an integrated shield wire of a composite coaxial cable wire can be soldered to the grounding land 36. The grounding land 36 is connected, via a grounding lead wire 36a, to an area of the electric connector 10 which has a grounding potential, for example, the shield frame 19 or the shield cap 20.

The signal wires constituting the cable wire 29 for use in the endoscope comprise solid wires and coaxial wires having relatively small line diameters. When the cable wires 29 with a small line diameter are soldered to the connection land 37, 38 on the cable wire connection portion 28x of the cable wire connector 28, a tensile force exerted on the vicinity of the soldered area of the cable wire 29 is likely to break the solid wires or coaxial wires in the cable wire 29. Among the electric wires constituting the cable wire 29, the integrated shield is relatively thick and robust. Thus, soldering the integrated shield to the grounding land 36 prevents a force from being exerted directly on the solid wires or coaxial wires in the cable wire 29 even with a tensile force applied to the cable wire 29. This makes the cable wire 29 unlikely to be broken.

A terminal portion 39 is formed at a distal end of the connection terminal portion 28y and comprises a plurality of terminal pieces 39a arranged at equal intervals and electrically connected to the connection lands 37, 38 via connection patterns (not shown). The terminal portion 39, provided in the connection terminal portion 28y and comprising the plurality of terminal pieces 39a, is shaped for insertion and installation in the connector 27, provided in the connector circuit board 26, described above.

With a plurality of solid wires or coaxial wires constituting the scope connector signal wire 30a, operation portion signal wire 30b, or insertion portion signal wire 30c of the cable wire 29 connected to the connection lands 37, 38 on the cable wire connection portion 28x of the cable wire connector 28, the cable wire connection portion 28x can be held generally cylindrical by attaching the I-shaped kerf 40a at one end portion of the cable wire connection portion 28x to the C-shaped kerf 40b at the other end portion of the cable wire connection portion 28x. That is, the kerfs 40a, 40b constitute a holding portion that holds the cable wire connection portion 28x cylindrical.

That is, the terminal portion 39 of the connection terminal portion 28y is inserted and installed in the connector 27, provided in the connector circuit board 26 in the shield frame 19 of the electric connector 10. The cable wire connection portion 28x is then deformed into a cylindrical shape, which is held by the holding portion including the C- and I-shaped kerfs 40a, 40b. Thus, the cable wire connector 28 having the connection lands 37, 38 arranged at large intervals can be accommodated in the small space in the shield frame 19.

Further, when the terminal portion 39 of the connection terminal portion 28y is inserted into the connector 27, the connection terminal portion 28y is bent toward the inner periphery of the cylindrically deformed cable wire connection portion 28x. This enables a reduction in the length of the cable wire connector 28 placed inside the shield frame 19, allowing the cable wire connector 28 to be housed in the small space in the shield frame 19.

A first variation of the cable wire connector 28 will be described with reference to FIG. 7. FIG. 7 shows that a 30m composite cable having a plurality of coaxial wires is connected to a cable wire connector 28' in accordance with the first variation. That is, FIG. 7 shows an integrated shield wire of the 30 m composite cable connected to a grounding land 36', shield wires of coaxial wires of the 30 m composite cable connected to the connection lands 38'a to 38'n, and core wires connected to connection lands 37'a to 37'n.

A cable wire connector 28' is different from the cable wire connector 28, described above with reference to FIG. 6, in the shape of the kerfs 40a, 40b, formed at the respective ends of the cable wire connection portion 28x and constituting the holding portion, and in the shape of the terminal portion 39, provided at the distal end of the connection terminal portion 28y.

A T-shaped cut-in hole 40'a is formed at one end of a cable wire connection portion 28'x of a cable wire connector 28' in accordance with the first variation. A hook-shaped portion 40'b shaped generally like an isosceles triangle is formed at the other end of the cable wire connection portion 28'x and has a connection piece provided on the bottom side of the triangular shape and having a predetermined width. The cable wire connection portion 28'x can be held generally cylindrical by inserting the isosceles triangular shape of the hooked portion 40'b into a wider portion of a T-shaped cut-in hole 40'a and setting the connection piece of the hooked portion 40'b in a narrower portion of the T-shaped cut-in hole 40'a.

Further, a distal end of the connection terminal portion 28'y has a terminal portion 39' comprising a plurality of terminal pieces 39'a and a guide piece 39'b extending parallel to the terminal pieces 39'a, serving as a guide portion. The guide piece 39'b is formed to be relatively narrower than the plurality of terminal pieces 39'a. When the terminal portion 39' is installed in the connector 27, the guide piece 39'b is inserted into a guide piece receptacle formed in the connector 27 (not shown) or extends along a guide piece guiding groove formed on the outside of a housing of the connector 27. The presence of the guide piece 39'*b* prevents the terminal portion 39' from being mistakenly turned upside down to install in the connector 27 during installation.

Moreover, although not shown, the connection terminal portion 28*y*, 28*y*', shown in FIGS. 6 and 7, is formed to be wider than the terminal portion 39, 39', comprising the plurality of terminal pieces 39*a*, 39*a*'. When the terminal portion 39, 39'*y* is appropriately installed in the connector 27 by the connection terminal portion 28*y*, 28*y*', the step portion between the connection terminal portion 28*y*, 28*y*' and the terminal portion 39, 39'*y* abuts against the surface of the connector 27. When the connection terminal portion 28*y*, 28*y*' is wider than the terminal portion 39, 39', determining that the connection terminal portion 28*y*, 28'*y* is abutted against the surface of the connector 27 allows the operator to recognize that the terminals portion 39, 39' has been appropriately installed in the connector 27.

Further, an index 39*x* is provided in the vicinity of the terminal portion 39 of the surface of the connection terminal portion 28*y*, shown in FIG. 6, to indicate the position of the outside of the distal end of the connector 27 located when the terminal portion 39 is appropriately installed in the connector 27. The index 39*x* makes it possible to prevent the terminal portion 39 of the cable wire connector 28 from being turned upside down when installed in the connector 27 and to check how the terminal portion 39 is installed in the connector 27.

In the above description, the core wires of solid or coaxial wires are connected to the connection lands 37, 37' on the cable wire connector 28, 28', shown in FIGS. 6 and 7 and the shield wires of coaxial wires are connected to the connection lands 38, 38'. However, changing the connection pattern of the connection lands 37, 37' 38, 38' allows the core wires of solid or coaxial wires to be connected to the connection lands 38, 38', while allowing the shield wires of coaxial wires to be connected to the connection lands 37, 37'. That is, the electric wires to be connected to the connection lands 37, 37', 38, 38' and the connection patterns are set in accordance with the type, thickness, and number of the solid and coaxial wires connected to the cable wire connectors 28, 28'. Further, the intervals appropriate for a soldering operation are set for the connection lands 37, 37', 38, 38' in accordance with the types and thickness of the solid and coaxial wires connected to the connection lands 37, 37', 38, 38'.

As described above, each of the cable wire connectors 28, 28' is T-shaped and is formed of a flexible circuit board. The plurality of connection lands 37, 37' 38, 38' are provided on the horizontally long planar cable wire connection portions 28*x*, 28'*x* at intervals that allow solid and coaxial wires to be easily soldered. Further, the terminal portions 39, 39', comprising the plurality of relatively narrow terminal pieces 39*a*, 39'*a*, are provided in the connection terminal portions 28*y*, 28'*y* connected, via the connection patterns, to the connection lands 37, 37', 38, 38', provided on the cable wire connection portions 28*x*, 28'*x*.

This allows the operation of soldering the plurality of solid and coaxial wires of the cable wire 29 to the cable wire connection portions 28*x*, 28'*x* to be two-dimensionally performed easily. Further, when the cable wire connector 28, 28' is connected to the connector circuit board 26 and accommodated in the shield frame 19, the cable wire connection portion 28*x*, 28*x*' and the connection terminal portion 28*y*, 28*y*' can be deformed for accommodation. This facilitates the operation of assembling the electric connector 10.

Now, a second variation of the cable wire connector 28 will be described with reference to FIGS. 8 and 9. As shown in FIG. 8, a cable wire connector 28" in accordance with a second variation is formed of a flexible circuit board like a general rectangle. The cable wire connector 28" has a cable wire connection portion comprising connection lands 37" arranged in a substantially central portion at equal intervals and to which core wires of coaxial wires are connected and connection lands 38" to which shield wires of coaxial wires and solid wires are connected. Further, the cable wire connector 28" has a rectangular slit 40" formed at a distal end thereof and serving as a locking portion and a terminal portion 39" extending from the rectangular slit 40" and having a terminal piece. Furthermore, a cable wire fixing piece 38"*z* extends from a proximal end of the cable wire connector 28".

FIG. 8 shows an example in which the connection land 38" is composed of a connection land 38"*x* comprising three connection lands to which solid wires are connected and a connection land 38"*y* comprising four connection lands to which shield wires of coaxial wires are connected.

With reference to FIG. 9, description will be given of the state in which the cable wire connector 28" connects to a composite coaxial cable 30*n* comprising three solid wires 30*x* and four coaxial wires 30*y*. The three solid wires 30*x* of the composite coaxial cable 30*n* are soldered to the respective three connection lands of the connection land 38"*x*. The shield wires of the four coaxial wires 30*y* are soldered to the respective four connection lands of the connection land 38"*y*. Moreover, the core wires of the four coaxial wires 30*y* are soldered to the respective connection lands of the connection land 37".

Further, the composite coaxial cable 30*n* is fixed to the cable wire fixing piece 38"*z* of the cable wire connector 28" via a heat-shrinkable tube 38"*t*.

Thus, when the terminal portion 39" of the cable wire connector 28" to which the plurality of solid wires 30*x* and coaxial wires 30*y*, constituting the composite coaxial cable 30*n*, are connected is inserted into the connector 27 for connection, the outer periphery of the connector 27 is fitted into the rectangular slit 40". This prevents the cable wire connector 28" from slipping out easily from the connector 27.

Further, an index 39"*x* is provided in the vicinity of the terminal portion 39" of the surface of the cable wire connector 28" to indicate the position of the end portion of the connector 27 located when the terminal portion 39" is appropriately installed in the connector 27 down to a predetermined position. The index 39"*x* makes it possible to easily distinguish the front surface of the cable wire connector 28" from its back surface and to determine, after the terminal portion 39" is installed in the connector 27, whether or not the terminal portion 39" is appropriately installed in the connector 27.

The number of the connection lands in the connection land 37", 38" of the cable wire connector 28" in accordance with the second variation as well as the type of the wires connected to the connection lands are only illustrative. The number and the type are freely set in accordance with the type, thickness, and number of the wires constituting the composite coaxial cable 30*n* connected to the cable wire connector 28".

When the widthwise dimension of the general rectangle of the cable wire connector 28" in accordance with the second variation is equal to or smaller than, for example, the inner diameter of an armor of the universal cord 110 or the insertion portion 108, the cable wire 29 to which the cable wire connector 28" is connected can be pulled out from and then inserted back into the universal cord 110 and the insertion portion 108. Thus, the operation of replacing the armor of the universal cord 110 and the insertion portion 108 does not require the operation of disconnecting the cable wire connector 28" from the cable wire 29 and then soldering the cable wire connector 28" back to the cable wire 29 and can be performed simply by removing the cable wire connector 28" from the connector 27.

Description will be given of a method of assembling the connector circuit board 26 and the cable wire connector 28, provided on the cable wire 29, to the electric connector 10, having the solid wire pins 23 and the coaxial pins 24, described above.

As described above with reference to FIG. 5, the base 11 has the plurality of solid wire pins 23 with the step portions 23f provided at the same height position and the plurality of coaxial pins 24 with the step portions 43c provided at the same height position, and is placed on the workbench so that the solid wire pins 23 and the coaxial pins 24 extend perpendicularly with the terminal portions of the pins 23 and 24 located above.

The through-holes 52a and 53a in the solid wire and coaxial shield pin lands 52 and 53 on the first circuit board portion 26a of the connector circuit board 26 with the connectors 27a to 27c mounted thereon are inserted around the perpendicularly extending solid wire pins 23 and the coaxial pins 24. The first circuit board portion 26a of the connector circuit board 26 with the solid wire pins 23 and the coaxial pins 24 placed therein is two-dimensionally installed on the plurality of solid wire pins 23 by abutting against the step portions 23f thereof. When the solid wire pins 23 and the coaxial pins 24 are inserted into the through-holes 52a and 53a in the solid wire and coaxial shield pin lands 52 and 53 on the first circuit board portion 26a of the connector circuit board 26, the front surface (see FIG. 3A) of the connector circuit board 26 is directed toward the circuit board 16 in the base 11.

After the first circuit board portion 26a of the connector circuit board 26 is installed on the solid wire pins 23 and the coaxial pins 24, provided in the base 11, the lands 52b are soldered to the solid wire pins 23 placed in the through-holes 52a in the solid wire pin lands 52 (P1 to P19) in the central portion of the first circuit board portion 26a. Once the solid wire pin lands 52 and the solid wire pins 23 are soldered together, the lands 53b are soldered to the shield portions 41 of the coaxial pins 24 placed in the through-holes 53a in the coaxial shield pin lands 53 (P21 to P25).

That is, the first circuit board portion 26a of the connector circuit board 26 is two-dimensionally installed with respect to the perpendicularly extending solid wire pins 23 and coaxial pins 24. The operation of soldering the solid wire pins 23 and the coaxial pins 24 to the first circuit board portion 26a of the connector circuit board 26 is a first circuit board-portion connecting step of sequentially soldering the solid wire pin lands 52 provided in the central portion of the first circuit board portion 26a from the center toward outer periphery of the first circuit board portion 26a (toward the outer edge of the first circuit board portion 26a), and after all these solid wire pin lands 52 are soldered, soldering the coaxial shield pin lands 53 provided on the outer periphery of the first circuit board portion 26a.

The first circuit board portion connecting step sequentially performs soldering from the pin lands provided in the center of the first circuit board portion 26a toward those provided in the outer periphery of the first circuit board portion 26a. This facilitates the soldering operation to improve efficiency. In particular, since the lands 53b of the coaxial shield pin lands 53 are provided closer to the outer edge of the first circuit board portion 26a than the through-holes 53a, this allows the operation of soldering the lands 53b to side surfaces of the shield portions 41 of the coaxial pins 24 to be performed from the outer edge of the first circuit board portion 26a, facilitating the operation of soldering the coaxial pins 24 to the coaxial shield pin lands 53.

After the first circuit board portion connecting step is executed to solder the solid wire pin lands 52 (P1 to P19) and coaxial shield pin lands 53 (P21 to P25) on the first circuit board portion 26a, the connector circuit board 26 is bent so that the first circuit board portion 26a and second circuit board portion 26b on the back surface (see FIG. 3B) of the connector circuit board 26 lie opposite each other. The core wire portions 43 of the coaxial pins 24 connected to the coaxial shield pin lands 53 on the first circuit board portion 26a are thus inserted into the respective through-holes 55a in the coaxial core wire pin lands 55 (P31 to P35) on the second circuit board portion 26b. The second circuit board portion 26b of the connector circuit board 26 with the core wire portions 43 of the coaxial pins 24 placed therein is two-dimensionally abutted against and then soldered to the step portions 43c of the core wire portions 43 of the plurality of coaxial pins 24.

That is, the second circuit board portion 26b of the connector circuit board 26 is two-dimensionally installed with respect to the perpendicularly extending coaxial pins 24. A second circuit board portion connecting step involves soldering the two-dimensionally installed second circuit board portion 26b of the connector circuit board 26 to the coaxial core wire pin lands 55 provided on the outer periphery of the second circuit board portion 26b.

After the first and second circuit board portion connecting steps are executed to attach the connector circuit board 26 to the solid wire pins 23 and coaxial pins 24, provided in the base 11, a cable wire connector installing step is executed to install the cable wire connectors 28a to 28c of the scope connector signal wire 30a, operation portion signal wire 30b, and insertion portion signal wire 30c of the cable wire 29, in the connectors 27a to 27c, respectively, as shown in FIG. 1. To be installed in the connectors 27a to 27c, respectively, on the connector circuit board 26 the cable wire connectors 28a to 28c are held deformed so as to be accommodated in the shield frame 19. Subsequently, the shield frame 19 is threadably fitted into the base 11, and the shield cap 20 is attached to the shield frame 19. The cable wire 29 is fixed by a cable wire fastening plate 21. This completes the assembly of the parts to the electric connector 10.

After the cable wire connectors 28a to 28c are installed in the connectors 27a to 27c, respectively, on the connector circuit board 26, the grounding lead wire 36a connected to the cable wire connector 28, 28', described with reference to FIGS. 6 and 7 and comprising the cable wire connectors 28a to 28c, is threadably fixed to the shield cap 20, located at the proximal end of the shield frame 19. Fixing the grounding lead wire 36a to the shield cover 20 electrically connects the shield pattern of the cable wire connectors 28a to 28c to the integrated shield of the cable wire 29, which is a composite cable, thus enhancing the grounding state. This improves electromagnetic compatibility (hereinafter also referred to as EMC).

As described above, the operation of assembling the electric connector 10 in accordance with the present embodiment involves two-dimensionally installing the connector circuit board 26 with respect to the base 11 with the solid wire pins 23 and the coaxial pins 24 perpendicularly placed therein. This enables the solid wire pins 23 and the coaxial pins 24 to be two-dimensionally soldered to the connector circuit board 26. Thus, this operation is easier and offers higher working efficiency than the conventional three-dimensional operation of soldering the solid wires 155 and the coaxial wires 156 coaxially to the solid wire pins 152 and the coaxial pins 154 for connection.

Moreover, soldering of the solid wire pins 23 and the coaxial pins 24 to the lands 52b, 53b, located around the periphery of the through-holes 52a, 53a in the first circuit board portion 26a, can be sequentially performed from the central portion toward outer edge of the first circuit board portion 26a or in order of the solid wire pins 23 and the coaxial pins 24. This facilitates the operation of soldering the connector circuit board 26 to the solid wire pins 23 and the coaxial pins 24.

In the above description, the lands 53b of the coaxial shield pin lands 53, formed on the first circuit board portion 26a of the back surface (see FIG. 3B) of the connector circuit board 26, are each provided on a part of the corresponding through-hole 53a which is closer to the outer edge of the first circuit board portion 26a. However, the land 53b may be formed all along the periphery of the through-hole 53a.

Now, description will be given of the procedure of an operation of checking the electronic endoscope having the electric connector 10 for an electrical error occurring in the endoscope and repairing the defective component.

To determine which component of the electronic endoscope is defective, the cable wire fastening plate 21 and the shield cap 20, which fasten the cable wire 29, are removed and the shield frame 19 is removed from the base 11. Then, the cable wire connectors 28a to 28c, provided on the scope connector signal wire 30a, operation portion signal wire 30b, and insertion portion signal wire 30c of the cable wire 29, are removed from the connectors 27a to 27c on the connector circuit board 26.

The cable wire connectors 28a to 28c removed from the respective connectors 27a to 27c on the connector circuit board 26 are connected to respective inspection jigs to perform inspections to determine which component is defective. For example, the cable wire connector 28a connected to the scope connector signal wire 30a is connected to a jig that checks the transmission and reception status of dimming signals transmitted to and received from the light source device 103. The cable wire connector 28b connected to the operation portion signal wire 30b is connected to a jig that checks the transmission and reception status of switch signals transmitted to and received from the image processing system switches, which are electric parts provided on the operation portion 109. The cable wire connector 28c connected to the insertion portion signal wire 30c is connected to a jig that checks the performance and operation of the image pickup unit including the CCD 115. This makes it possible to determine whether or not an error is occurring in each of the cable wire connectors and where the error is occurring. If the operation portion 109 has any electric part other than the image processing system switches which provides a predetermined function different from those of the switches, the operation portion signal line 30b is connected to a jig that checks the performance and operation of the electric part to which the operation portion signal wire 30b is connected. Further, if the distal end of the insertion portion 108 has any electric part other than the image pickup unit including the CCD 115 which provides a predetermined function different from those of the image pickup unit, for example, an LED, the insertion portion signal line 30c is connected to a jig that checks the performance and operation of the electric part to which the insertion portion signal wire 30c is connected.

Figure 11:
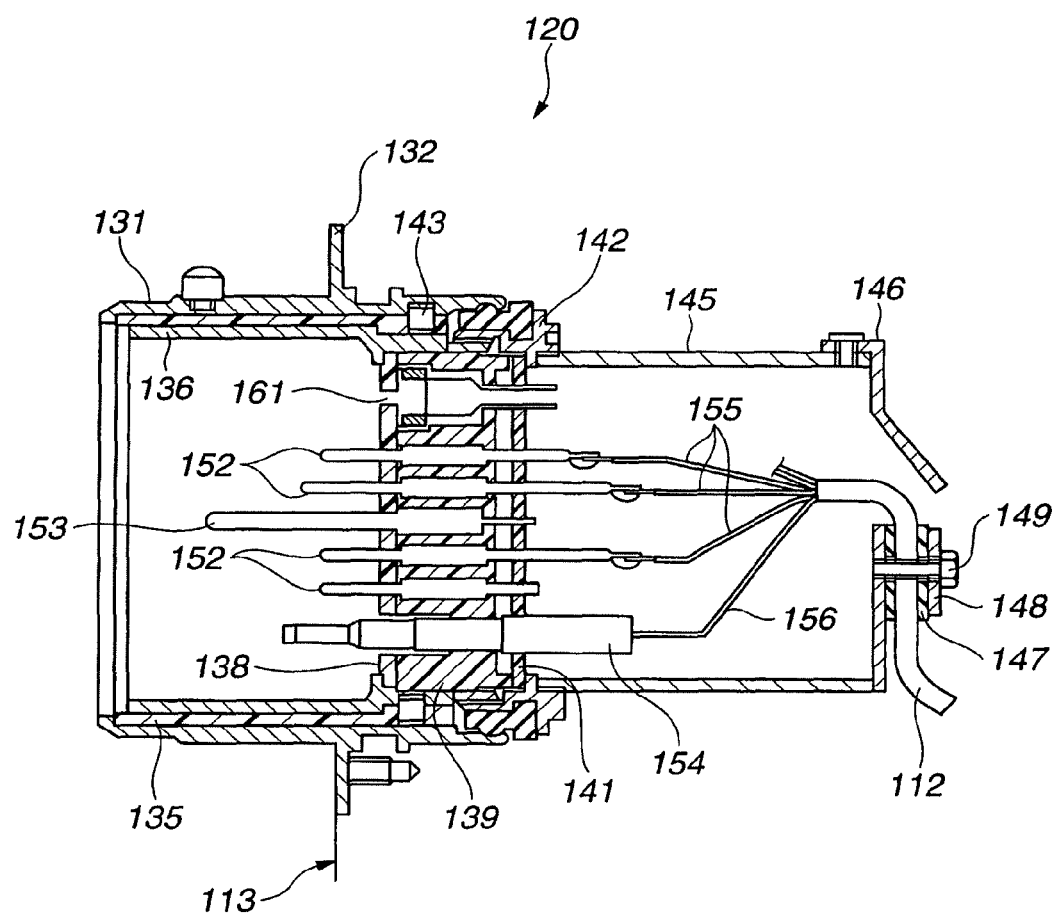
FIG. 11 is a vertical sectional view showing the configuration of an electric connector for a conventional endoscope.

The present embodiment thus eliminates the need for the complicated operation of disconnecting the solid wires 155 and coaxial wires 156 of the cable wire 112 soldered to the solid wire pins 152 and coaxial pins 154 in the base 131 and soldering the disconnected solid wires 155 and coaxial wires 156 again to inspection jigs as described with reference to FIG. 11 for the prior art. The present embodiment requires only an easy operation of only connecting the cable wire connectors 28a to 28c removed from the connectors 27a to 27c on the connector circuit board 26 to inspection jigs.

Further, the electric connector 10 with the cable wire connectors 28a to 28c removed from the connectors 27a to 27c on the connector circuit board 26 is checked for connections to the solid wire pins 23, the coaxial pins 24, and the connector circuit board 26. If any defect is found in any of the solid wire pins 23 or the coaxial pins 24 or in the connection to any of the solid wire pins 23, the coaxial pins 24, or the connector circuit board 26 and the connector circuit board 26 needs to be removed from the solid wire pins 23 and the coaxial pins 24. The removal operation can be easily achieved by performing an operation reverse to the assembly of the connector circuit board 26 described above.

That is, first, removal is made of the solder connecting the lands 55b of the coaxial core wire pin lands 55 on the second circuit board portion 26b of the connector circuit board 26 to the core wire portions 43 of the coaxial pins 24; the soldering operation is performed during the second circuit board portion connecting step for assembly. The core wire portions 43 of the coaxial pins 24 are then removed from the through-holes 55a.

Then, removal is made of the solder connecting the lands 53b of the coaxial shield pin lands 53, provided on the outer periphery of the first circuit board portion 26a, to the shield portions 41 of the coaxial pins 24; the soldering operation is performed during the first circuit board portion connecting step for assembly. Once the solder on the coaxial shield pin lands 53 is removed, the solder connecting the lands 52b of the solid wire pin lands 52 on the first circuit board portion 26a to the solid wire pins 23 is sequentially removed from the solid wire pin lands 52 on the outer periphery of the first circuit board portion 26a toward those in the central portion of the first circuit board portion 26a. Thus, the operation can be more easily and efficiently performed by sequentially removing the solder from the pin lands arranged on the outer periphery of the first circuit board portion 26a to those arranged in the central portion of the first circuit board portion 26a.

As described above, the present embodiment can provide an electric connector for an endoscope that makes it possible to simplify work operations such as the assembly, operation check, and repair of the electric connector to reduce the time required for the work operations, as well as the endoscope and a method for assembling the electric connector.

That is, the electric connector 10 has the connector circuit board 26 having the surface to which the solid wire pins 23 and the coaxial pins 24, connected to the video processor 106, an external instrument, and serving as connection terminals, are connected and the surface comprising the connector 27 to and from which the cable wire connector 28, connected to the end portion of the signal wire 30 of the cable wire 29 extending from the endoscope, is attached and removed. This enables the operation check and repair of the endoscope through a simple operation of only installing and removing the cable wire connector 28. Further, when the connector circuit board 26 is assembled to the electric connector 10, the solid wire pins 23 and the coaxial pins 24 can be connected to the connector circuit board 26 by two-dimensionally holding the connector circuit board 26 with respect to the solid wire pins 23 and the coaxial pins 24 and sequentially soldering the solid wire pins 23 and the coaxial pins 24 from those in the center of the connector circuit board 26 toward those on the outer periphery of the connector circuit board 26. This improves the efficiency of the operations of assembling and repairing the connector circuit board 26. Moreover, the cable wire 29 extending from the endoscope can be connected to the cable wire connector 28 by performing a soldering operation with the cable wire 29 two-dimensionally placed with respect to the cable wire connector 28. This improves the efficiency of the soldering operation.

Further, in the electric connector 10 for the endoscope in accordance with the present embodiment, the cable wire connector 28 for the scope connector signal wire 30a, operation portion signal wire 30b, insertion portion signal wire 30c, and the like of the cable wire 29 and the like as well as the connector circuit board 26, having the connector 27 to which the cable wire connector 28 can be connected, are provided in the scope connector 113 for the universal cord 110 having a space that can be shielded and blocked by the shield frame 19 and the shield cap 20. This improves electromagnetic compatibility.

Moreover, although the cable wire 29 of the scope connector signal wire 30a, operation portion signal wire 30b, insertion portion signal wire 30c, and the like swing in the universal cord 110 in response to the operation of the operation portion 109 or insertion portion 108 of the electronic endoscope 102. However, the swing of the cable wire 29 does not directly affect the cable wire connector 28 and the connector 27 of the connector circuit board 26 because a part of the cable wire 29 located in the vicinity of the cable wire connector 28 is fixed to the shield cap 20 via the cable wire fastening plate 21. This makes it possible to avoid the possible inadvertent removal of the cable wire connector 28 and the possible disconnection between the cable wire connector 28 and the signal wire 30.

The above embodiment of the present invention has been described taking the case in which the video processor 106, a signal processing device serving as an external instrument, is separated from the light source device 103. However, the video processor 106, a signal processing device, and the light source device 103 may be integrated into an external instrument.

Figure 10:
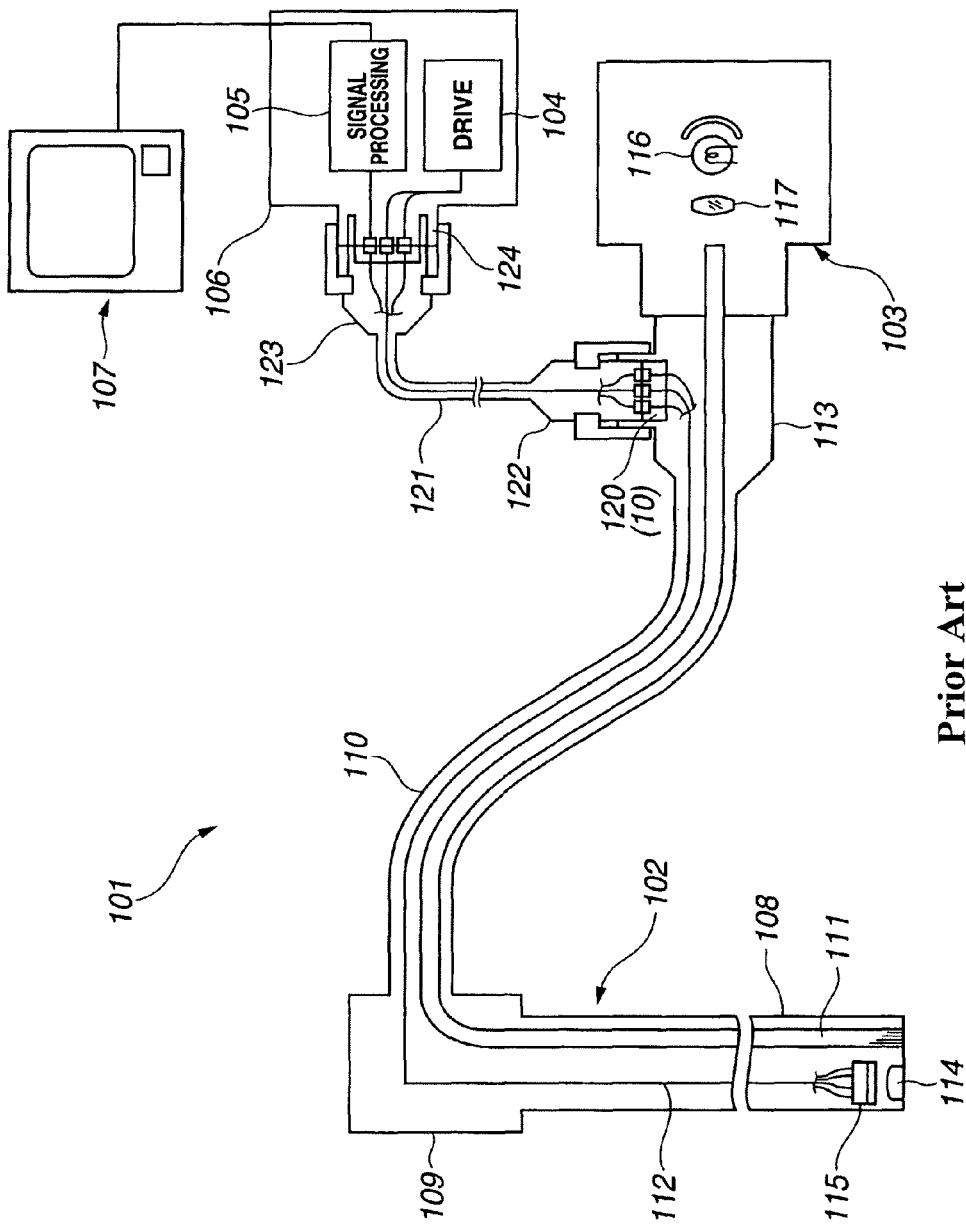
FIG. 10 is a conceptual diagram showing the concept of the configuration of a conventional electronic endoscope apparatus.

The electronic endoscope 102 using the conventional electric connector 120, described with reference to FIGS. 10 and 11, poses the following problems.

To replace any part of the electronic endoscope 102 using the conventional electric connector 120, for repair or the like, the cable wire 112 is disconnected from the solid wire pins 152 and the coaxial pins 154, and action required for the repair such as part replacement is then taken. Then, the end portion of the cable wire 112 is connected again to the solid wire pins 152 and the coaxial pins 154.

For example, if owing to inappropriate images, the image pickup unit, which provides functions for image pickup for the electronic endoscope 102 including the CCD 115, is checked for operation, the cable wire 112 is disconnected from the solid wire pins 152 and coaxial pins 154 in the electric connector 120. Subsequently, the cable wire 112 is connected to an inspection jig for the image pickup unit, which is then used to check the image pickup unit for operation and defects. If any defect is found in the image pickup unit, the defective part is replaced or repaired and the cable wire 112 is connected back to the solid wire pins 152 and coaxial pins 154 in the electric connector 120.

Further, if the image processing system switches provided on the operation portion 109 are checked for defects, the cable wire 112 is disconnected from the solid wire pins 152 and coaxial pins 154 in the electric connector 120 as is the case with the above operation check on the image pickup unit. Subsequently, the cable wire 112 is connected to an inspection jig for the switches, which is then user to check the switches for operation and defects. If any defect is found in any of the switches, the defective switch is replaced or repaired and the cable wire 112 is connected back to the solid wire pins 152 and coaxial pins 154 in the electric connector 120.

Further, the need to replace the armor of the universal cord 110 or the armor of the insertion portion 108 arises instead of part replacement or repair resulting from an electrical defect such as inappropriate images or a defective switch, the cable wire 112 is disconnected from the solid wire pins 152 and the coaxial pins 154 in the electric connector 120.

For example, if the armor of the universal cord 110 degraded by temporal changes is replaced with a new one, the cable wire 112 is disconnected from the solid wire pins 152 and coaxial pins 154 in the electric connector 120. The cable wire 112 is then pulled out from the operation portion 109 side of the universal cord 110. The pulled-out cable wire 112 is inserted into the armor of the new universal cord 110 and connected back to the solid wire pins 152 and coaxial pins 154 in the electric connector 120.

Further, if the armor of the insertion portion 108 degraded by temporal changes is replaced with a new one, the cable wire 112 is disconnected from the solid wire pins 152 and coaxial pins 154 in the electric connector 120. The disconnected cable wire 112 is pulled out from the operation portion 109 side of the armor of the universal cord 110. The cable wire 112 is further pulled out from the distal end side of the insertion portion 108 through the armors of the operation portion 109 and the insertion portion 108. The cable wire 112 pulled out from the operation portion 109 and the insertion portion 108 is inserted again through an armor of a new insertion portion 108. The cable wire 112 is further inserted back through the operation portion 109 and the universal cord 110 and then connected back to the solid wire pins 152 and coaxial pins 154 in the electric connector 120.

That is, if operation check, check for defects, or replacement and repair is performed on the image unit or switches of the electronic endoscope 102, connected to the conventional electric connector 120 via the cable wire 112, it is necessary to perform complicated, time-consuming work operations such as the disconnection of the cable wire 112 connected to the electric connector 120, the connection of the disconnected cable wire 112 to an inspection jig, and the re-connection of the cable wire 112 to the electric connector 120. Further, if the armor of the insertion portion 108 or the universal cord 110 is replaced, it is also necessary to perform complicated, time-consuming work operations such as the disconnection of the cable wire 112 connected to the electric connector 120, the pullout of the disconnected cable wire 112 from the armors of the universal cord 110 and the insertion portion 108, the re-insertion of the cable wire 112 into the armors of the new insertion portion 108 and the universal cord 110, and the re-connection of the cable wire 112 to the electric connector 120.

Further, the plurality of solid wire pins 152 and coaxial pins 154 in the electric connector 120 are provided in a limited area and thus arranged at relatively small intervals. The small intervals among the solid wire pins 152 and among the coaxial pins 154 make it difficult to perform the operation of disconnecting only the cable line 112 connected to the image pickup unit, from the solid wire pins 152 and the coaxial pins 154, or selectively disconnecting and then connecting only the cable wire 112 connected to the switches from and back to the solid wire pins 152 and the coaxial pins 154. Thus, to check the image pickup unit or any of the switches for operation and defects, it is desirable to disconnect all the cable wires 112 connected to the electric connector 120. Consequently, after the check for operation and defects, all the cable wires 112 connected to the image pickup unit or the switches must be connected back to the solid wire pins 152 and coaxial pins 154, arranged at the small pin intervals. This requires a complicated operation.

Moreover, the solid wire pins 152 and coaxial pins 154 in the electric connector 120 are provided parallel to the axial direction of the base 131 and perpendicularly to the cover member 138, the insulator 139, and the circuit board 141. Thus, to connect the cable wire 112 to the solid wire pins 152 and the coaxial pins 154, the electric connector 120 is installed so that the solid wire pins 152 and the coaxial pins 154 lie perpendicularly to a level workbench. The distal end portion of the cable wire 112 is connectively coaxially soldered to the perpendicularly extending solid wire pins 152 and coaxial pins 154. That is, in the operation of connecting the cable wire 112 to the solid wire pins 152 and the coaxial pins 154, care needs to be always taken so as to prevent the situation in which the cable wire 112 bends at a position close to the soldered part to come into contact with the adjacent solid wire pin 152 or coaxial pin 154 to prevent soldering of other cable wires 112, or a jig needs to be prepared which holds the cable wire 112 so as to prevent the cable wire 112 from being bent. Thus, much attention must be paid to the operation of connecting the cable wire 112 to the plurality of solid wire pins 152 and coaxial pins 154, requiring a long operation.

Further, the solid wire pins 152 and the coaxial pins 154 may be connectively soldered to the solid wires 155 and coaxial wires 156 of the cable wire 112 via electronic parts such as diodes or resistors. In this case, care must be taken for the possible bending not only of the cable wire 112 but also of leads of the electronic parts. This further makes the operation of connecting the cable wire 112 to the plurality of solid wire pins 152 and coaxial pins 154 more complicated and time-consuming.

Thus, the repair operation involves disconnecting the plurality of electric wires of the cable wire 112 connected to the solid wire pins and coaxial pins arranged at the small intervals and then connecting the electric wires back to the solid wire pins and coaxial pins directly or via an electronic part; the repair operation itself is very complicated and must be carefully performed over time.

Further, for checks for operation and defects described above, the insulating coating on the distal end of the cable wire 112 is peeled off and soldered to an inspection jig in order to connect the cable wire 112 to the inspection jig. The distal end of the cable wire 112 that has already been checked for operation and defects using the inspection jig is disconnected to clear the connection to the inspection jig. The insulation coating is peeled off from the distal end of the cable wire 112 disconnected from the inspection jig so as to allow the distal end to be connectively soldered back to the solid wire pins 152 and coaxial pins 154 in the electric connector 120. Thus, the distal end of the cable wire 112 is cut for every check for operation and defects, reducing the entire length of the cable wire 112. The reduced length of the cable wire 112 makes checks for operation and defects as well as a re-connection operation difficult and time-consuming.

However, the electronic endoscope using the electric connector 10 in accordance with the first embodiment makes it possible to simplify work operations such as the disassembly and assembly of the electric connector and the operation check and repair of electric parts of the electronic endoscope. This enables a reduction in the time required for the work operations.

For example, to disconnect the electric connector 10 from the cable wire 29, the cable wire connectors 28a to 28c are removed from the connectors 27a to 27c on the connector circuit board 26. Further, to connect the electric connector 10 back to the cable wire 29, the cable wire connectors 28a to 28c are inserted into the connectors 27a to 27c on the connector circuit board 26. This enables the operation of checking electric parts such as the image pickup unit including the CCD 115 and the image processing system switches to be performed without the need to disconnect the cable wire 29. That is, it is unnecessary to perform the complicated operation of disconnecting the solid wires 155 and coaxial wires 156 of the cable wire 112 soldered to the solid wire pins 152 and the coaxial pins 154 and then soldering the disconnected solid wires 155 and coaxial wires 156 back to the cable wire 112 as is the case with the conventional technique, as described above with reference to FIG. 11. Thus, the electronic endoscope using the electric connector 10 in accordance with the first embodiment makes it possible to simplify the operation of checking the electric parts of the electronic endoscope for operation, enabling a reduction in the time required for work operations.

Further, for example, to replace an electric part such as the image pickup unit including the CCD 115 or any of the image processing system switches, the disconnection and re-connection between the electric connector 10 and the cable wire 29 can be easily performed by inserting and removing the connector. Moreover, to replace an electric part, the following operation must be performed: the cable wire 29 connected to that electric part is disconnected from the cable wire connector 28, the electric part is repaired or replaced with a new one, and the cable wire 29 is then connected back to the cable wire connector 28. However, the operation of connecting the cable wire 29 to the cable wire connector 28 can be easily performed because soldering can be achieved with the cable wire 29 two-dimensionally placed with respect to the cable wire connector 28. Thus, the electronic endoscope using the electric connector 10 in accordance with the first embodiment makes it possible to simplify the operation of replacing the electric parts provided in the electronic endoscope, enabling a reduction in the time required for work operations.

Further, even if any of the solid wire pins 23, coaxial pins 24, and connector circuit board 26 in the electric connector 10 becomes defective and the electric connector 10 thus needs to be repaired, the electric connector 10 can be easily disconnected from the cable wire 29. This enables only the electric connector 10 to be disassembled and repaired without disconnecting the cable wire 29.

Therefore, the electronic endoscope using the electric connector 10 in accordance with the first embodiment can simplify work operations such as the assembly and disassembly of the electric connector, the operation check of electric parts of the electronic endoscope, and the repair of the electronic endoscope. This enables a reduction in the time required for the work operations.

Furthermore, the present embodiment eliminates the need for a soldering operation when the electric connector 10 is disconnected from and then connected back to the cable wire 29. This eliminates the need to cut the distal end of the cable wire for soldering for every check for operation and defects. This in turn prevents the cable wire from being shortened even with repeated checks for operation and defects. It thus becomes unnecessary to replace the cable wire which otherwise need not be replaced but which has been shortened as in the prior art.

Second Embodiment

Figure 12:
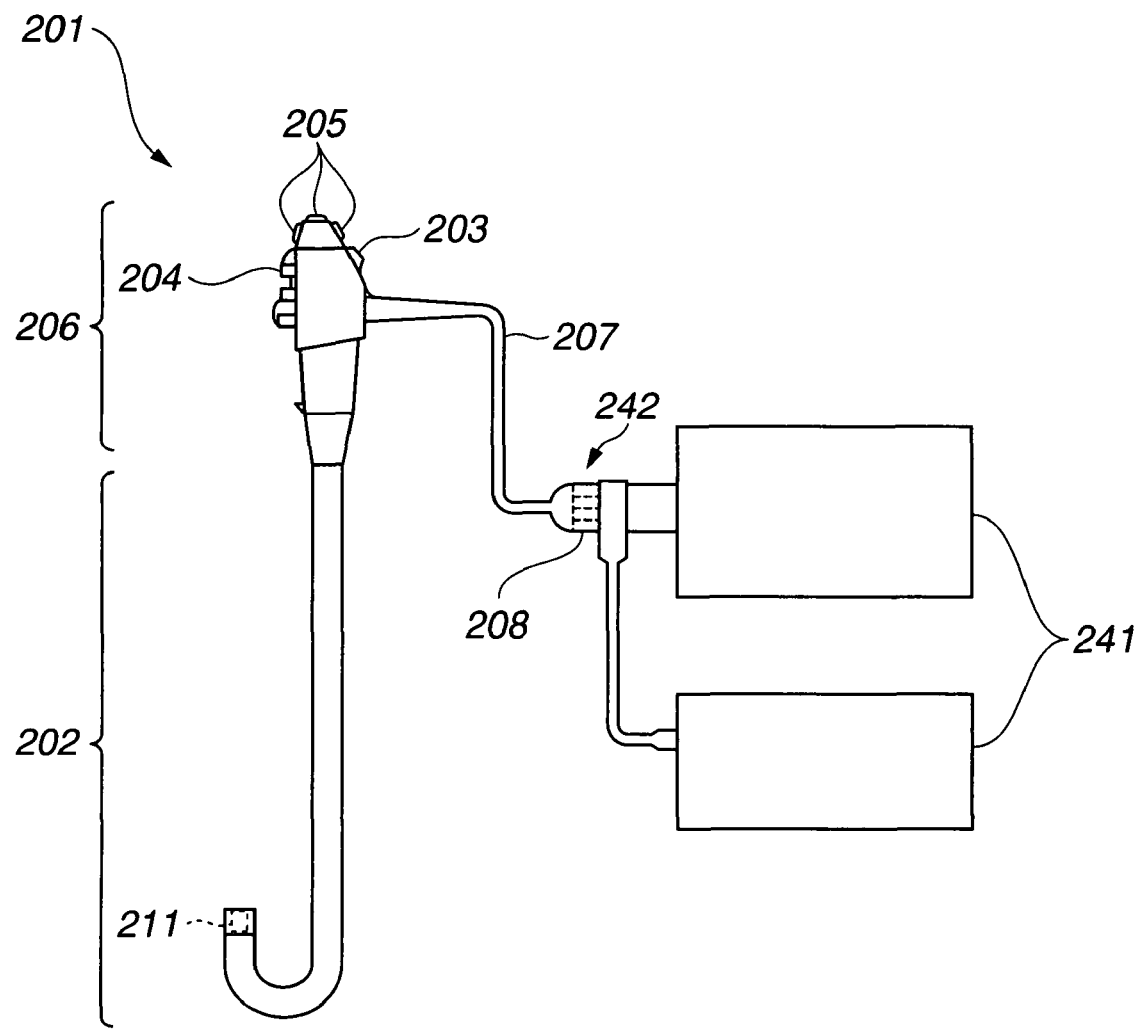
FIG. 12 is a diagram showing the general configuration of an electronic endoscope apparatus in accordance with a second embodiment.
Figure 13:
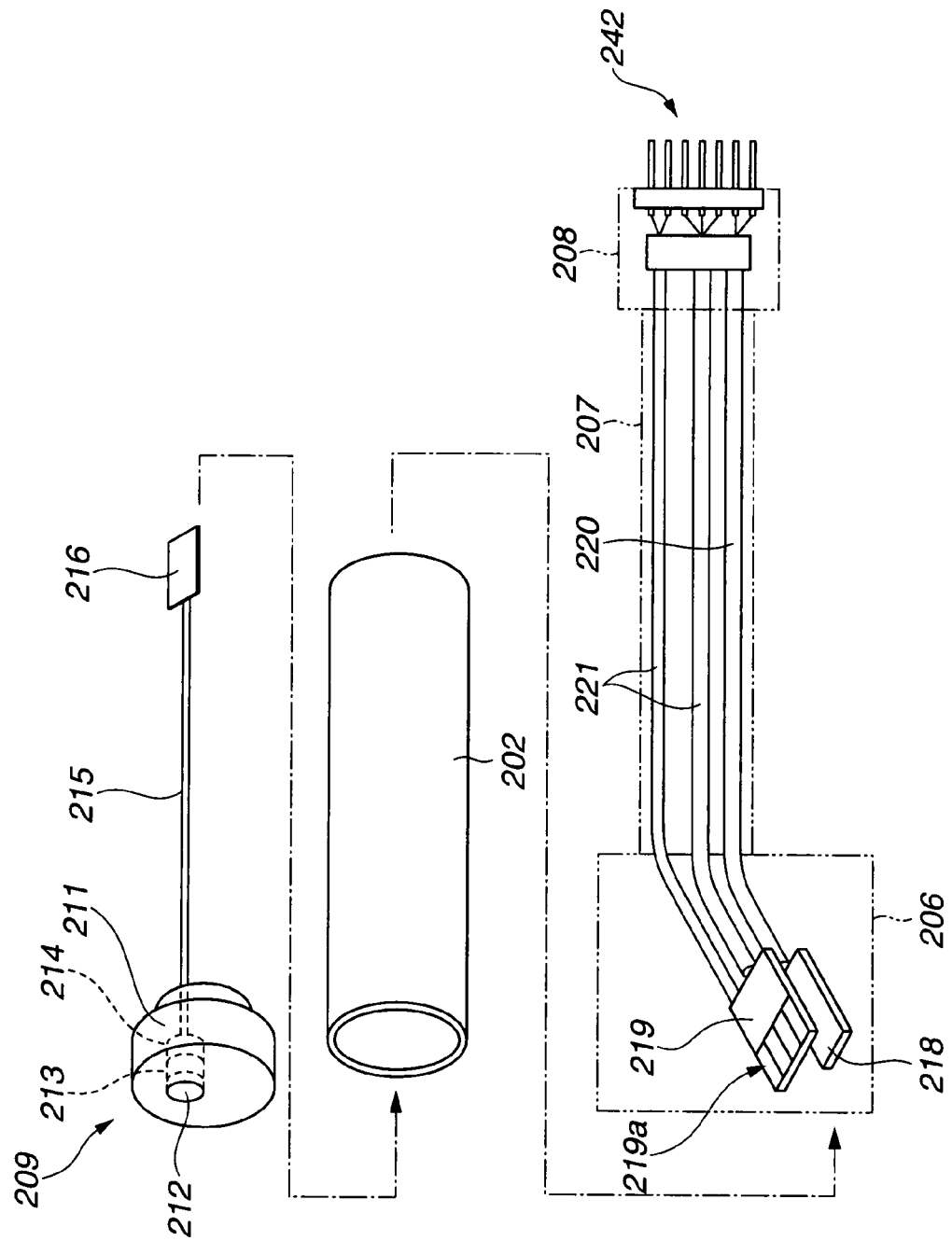
FIG. 13 is a diagram showing connections between an image pickup portion and an electric connector and signal wires in accordance with the second embodiment.
Figure 14:
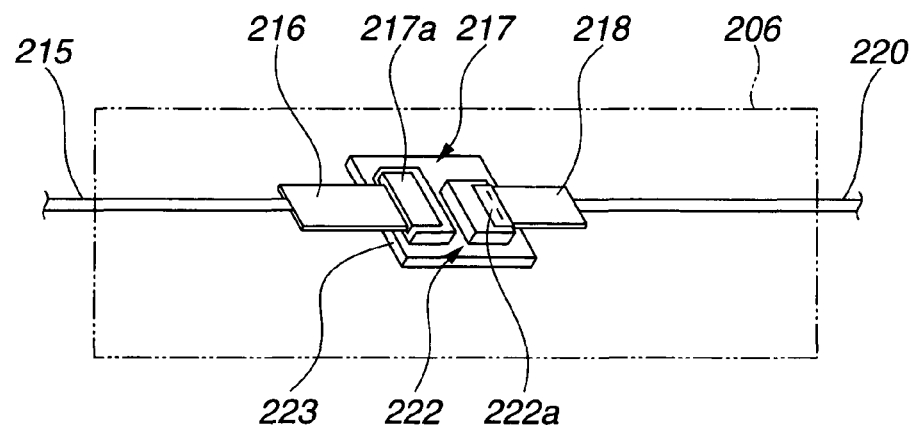
FIG. 14 is a partial enlarged perspective view showing the configuration of a connection member that connects the image pickup portion to the electric connector in accordance with the second embodiment.
Figure 15:
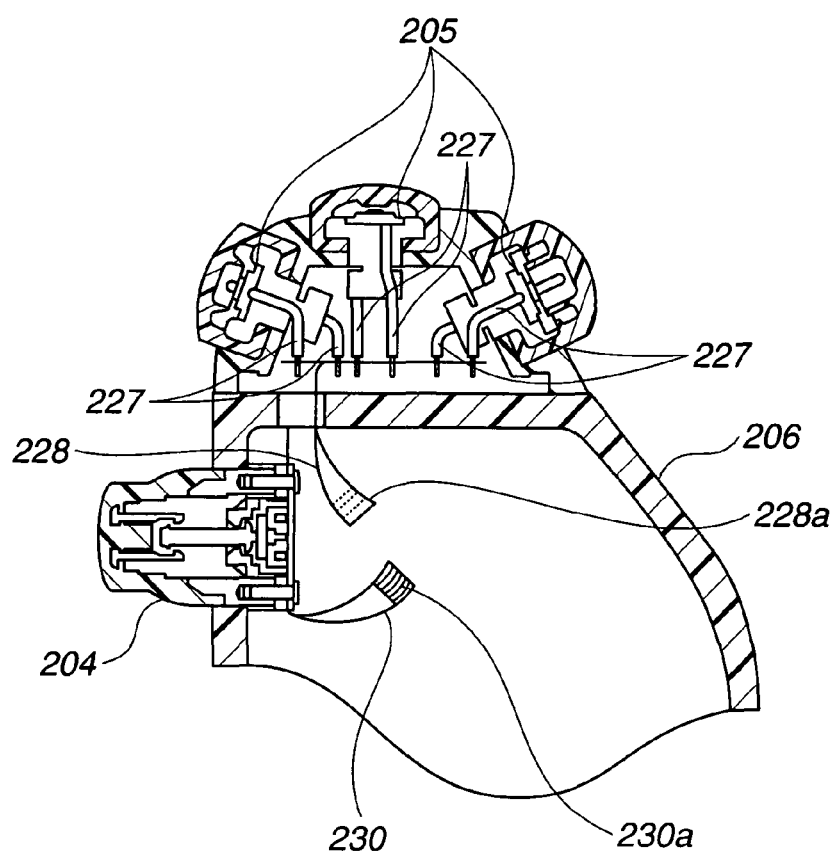
FIG. 15 is a partial sectional view showing an electric switch fixed to an operation portion in accordance with the second embodiment.
Figure 16:
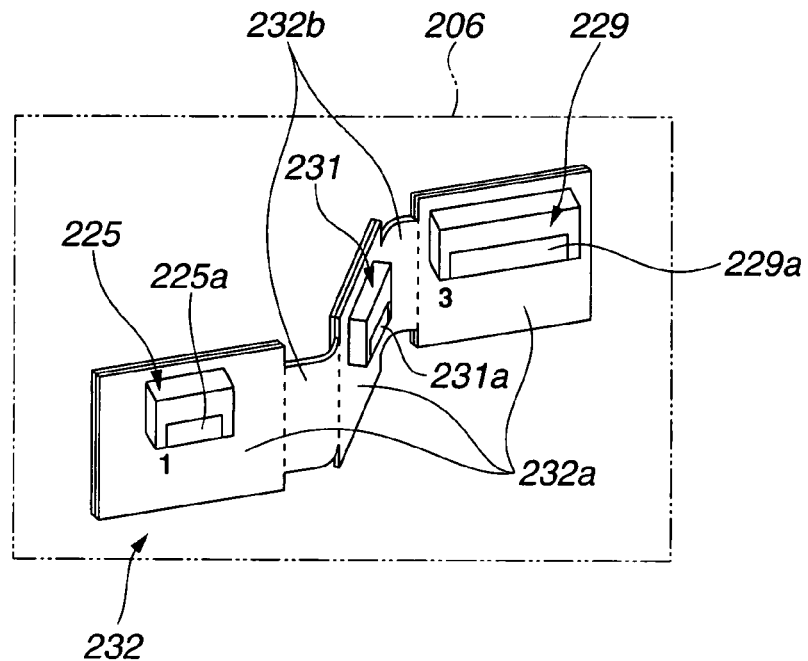
FIG. 16 is a partial enlarged perspective view showing the configuration of a connection member that connects the electric switch to the electric connector in accordance with the second embodiment.
Figure 17:
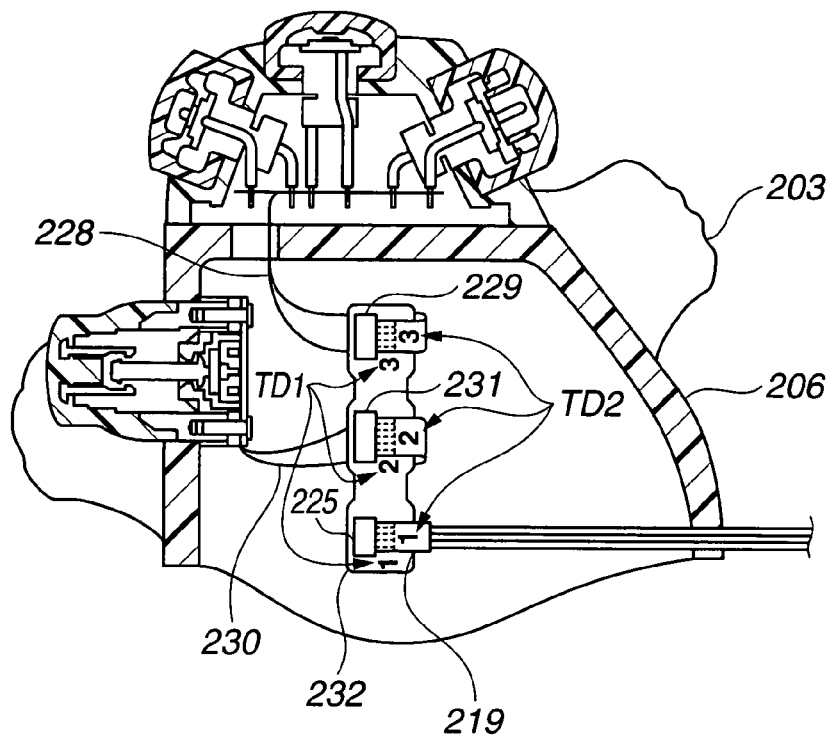
FIG. 17 is a partial sectional view illustrating the connection between the electric switch and the connection member in accordance with the second embodiment.
Figure 18:
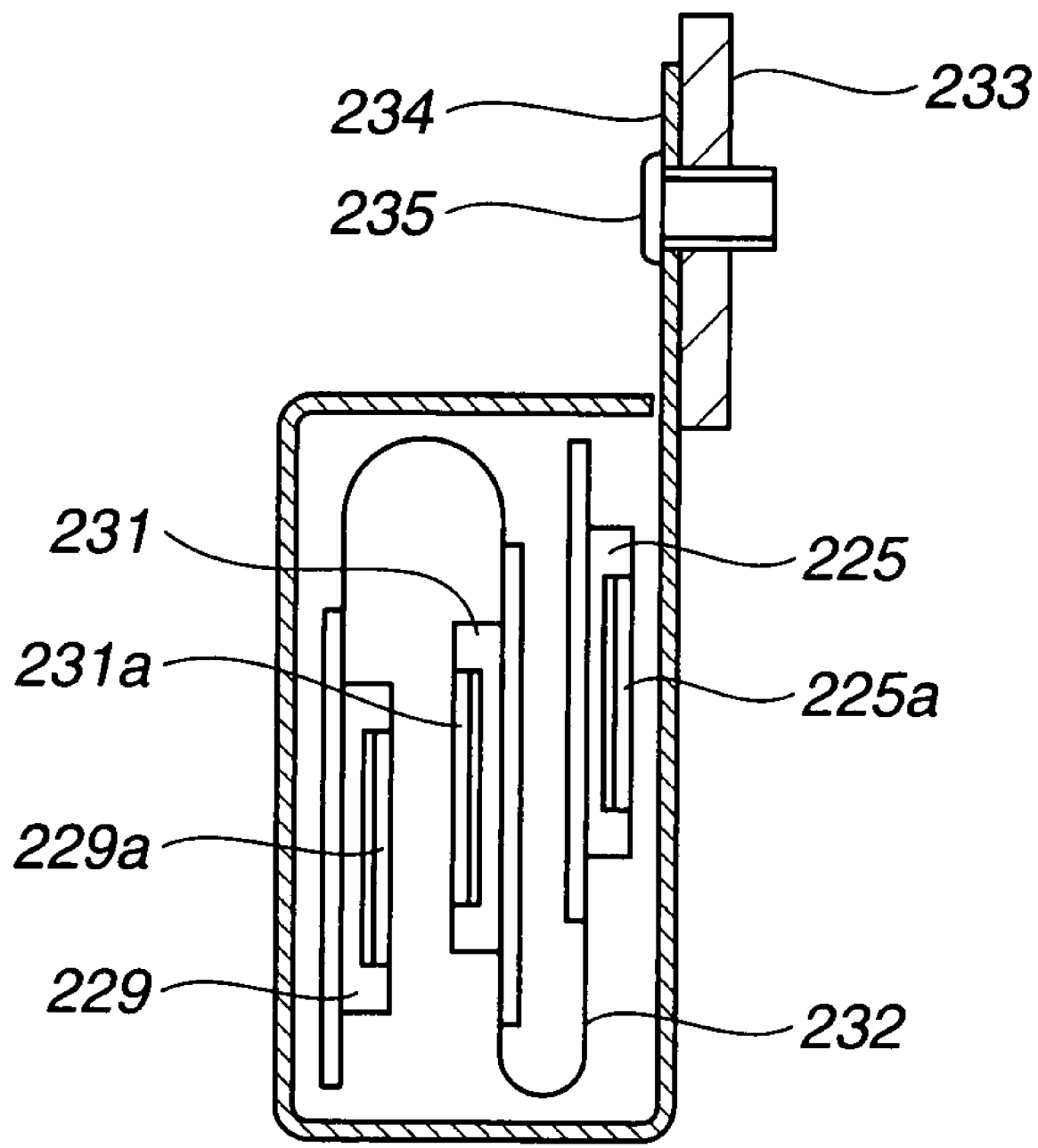
FIG. 18 is a partial enlarged sectional view showing a cross section of a metal housing in which the connection member in accordance with the second embodiment is housed.
Figure 19:
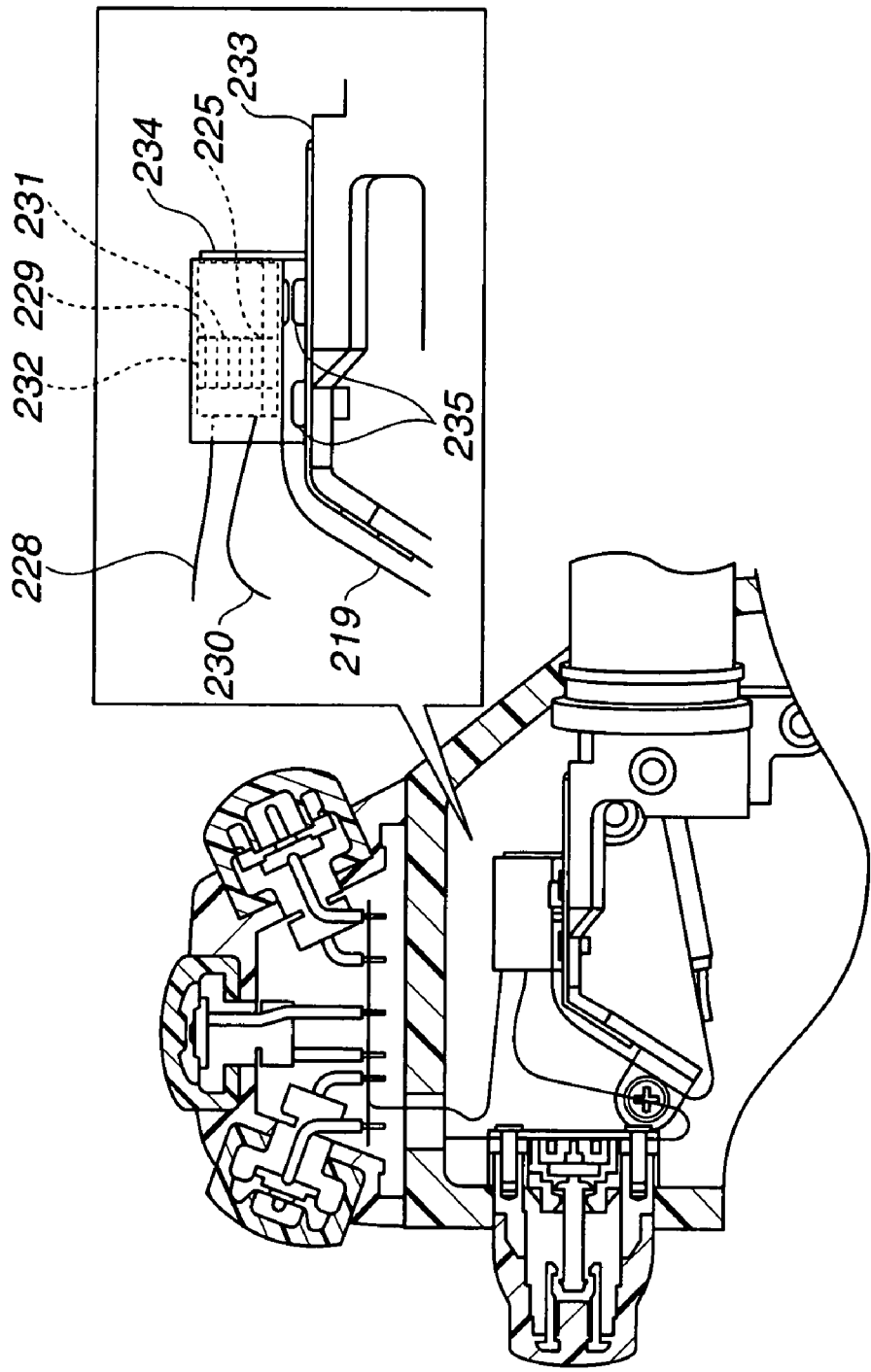
FIG. 19 is a partial sectional view showing how the connection member in accordance with the second embodiment is housed in the metal housing.

An embodiment of the present invention will be described with reference to the appropriate drawings. FIG. 12 is a diagram showing the general configuration of an electronic endoscope apparatus. FIG. 13 is a diagram showing the connection between an image pickup portion and an electric connector and signal wires. FIG. 14 is a partial enlarged perspective view showing the configuration of a connection member that connects the image pickup portion to the electric connector. FIG. 15 is a partial sectional view showing electric switches fixed to an operation portion. FIG. 16 is a partial enlarged perspective view showing the configuration of a connection member that connects the electric switch to the electric connector. FIG. 17 is a partial sectional view illustrating the connection between the electric switch and the connection member. FIG. 18 is a partial enlarged sectional view showing a cross section of a metal housing in which the connection member is housed. FIG. 19 is a partial sectional view showing how the connection member is housed in the metal housing.

As shown in FIG. 12, an electronic endoscope 201 in accordance with the present embodiment has an insertion portion 202 which is inserted into the body cavity and which has an image pickup portion 211 at a distal end portion thereof, an operation portion 206, a universal cord 207 that is a connection cable extending from the operation portion 206, and a scope connector 208 as an endoscope connector portion provided at a proximal end portion of the universal cord 207 for connection to an external instrument 241. The operation portion 206 has an operation knob 203 used to perform an operation for bending a bending portion at a distal end portion of the insertion portion 202, and electric switches 204 and 205 used to operate the external instrument 241, serving as an external apparatus. Further, the scope connector 208 has an electric connector 242 that is an electric contact portion and that electrically connects the electronic endoscope 201 to the external instrument 241.

The electronic endoscope 201 internally has a signal wire having one end connected to the electric connector 242 and the other end electrically connected to the image pickup portion 211 (this signal wire is hereinafter referred to as an insertion portion signal wire), and a signal wire having one end connected to the electric connector 242 and the other end electrically connected to the electric switches 204 and 205 (this signal wire is hereinafter referred to as an operation portion signal wire). In the embodiment of the present invention, the insertion portion signal wire and the operation portion signal wire are each divided into two pieces in the operation portion. The resulting two signal wires are each electrically connected to the appropriate parts via a connection member independent of the signal wire. The operation portion signal wires may be connected to another electric part provided in the operation portion 206 instead of the electric switches 204 and 205.

With reference to FIGS. 13 and 14, a detailed description will be given of the insertion portion signal wire, which connects the image pickup portion 211 to the electric connector 242.

As shown in FIG. 13, the image pickup portion 211, located at a distal end portion 209 of the insertion portion 202, has an objective optical system 212, a solid-state image pickup device 213 disposed at an image forming position behind the objective optical system 212 and comprising a CCD or the like, and a signal processing circuit 214 connected to the solid-state image pickup device 213. Further, a signal wire 215 that is a cable wire having one end connected to the image pickup portion 211 is placed in the insertion portion 202. The signal wire 215 extends into the operation portion 206 with a flexible circuit board (hereinafter referred to as an FPC) 216 connected to the other end of the signal wire 215. The FPC is composed of a film comprising a heat-resistant material, for example, polyimide, and a conductor circuit provided on the film. The FPC 216 has a linear conductor portion extending in direction in which the FPC 216 is inserted into a connector 217 of a connection member 223. The conductor portion is electrically connected to a plurality of conductor wires in the signal wire 215. The image pickup portion 211 has electronic or electric parts which provide a predetermined function, such as light emitting devices (for example, LEDs) that illuminate a subject. One end of the signal wire 215 may be connected to these electronic or electric parts.

A signal wire 220 that is a cable wire having one end connected to the electric connector 242 is placed inside the universal cord 207. The signal wire 220 extends into the operation portion 206 with the FPC 218 connected to the other end of the signal wire 220. The FPC 218 has a linear conductor portion extending in a direction in which the connection member 223 is inserted into a connector 222, described below. The conductor portion is electrically connected to a plurality of conductor wires in the signal wire 220.

As shown in FIG. 14, a connection member 223 is located inside the operation portion 206 and equipped with a connector 217 to which the FPC 216, provided at a proximal end of the signal wire 215, is connected and a connector 222 to which the FPC 218, provided at a distal end of the signal wire 220, is connected. The connection portion 223 is composed of an FPC having a circuit to which the connectors 217 and 222 are electrically connected together. Further, the connectors 217 and 222 have releasing mechanisms 217a and 222a, respectively.

FPCs 216 and 218 are inserted into openings in the connectors 217 and 222, respectively. The releasing mechanisms 217a and 222a are then placed in fixing positions to catch the FPCs 216 and 218. This operation allows the signal wire 215 to be connected to the image pickup portion 211 and the signal wire 220 to be connected to the electric connector 242 to be electrically connected together via the connection member 223. The insertion portion signal wire is composed of the signal wire 215, the signal wire 220, and the connection member 223.

Further, to prevent the FPCs and the connectors from being incorrectly connected together, the fitting width between the connector 217 and the FPC 216 to be inserted into the connector 217 is set different from that between the connector 222 and the FPC 218 to be inserted into the connector 222.

Now, with reference to FIGS. 12, 13, 15, 16, and 17, a detailed description will be given of the operation portion signal wire, which electrically connects the electric switches 204 and 205 to the electric connector 242.

In the endoscope 201 in accordance with the embodiment of the present invention, the proximal end of the insertion portion 202 is connected to a bottom surface of the operation portion 206, as shown in FIG. 12. Further, the universal cord 207 is connected to one side surface of the operation portion 206 having a side in contact with the surface of the operation portion 206 to which the insertion portion 202 of the operation portion 206 is connected, the side surface also crossing the above surface of the operation portion 206 at right angles.

The electric switch 204 is disposed on a surface of the operation portion 206 which lies opposite the surface of the operation portion 206 to which the universal cord 207 is connected. The electric switch 205 is disposed on a surface of the operation portion 206 which lies opposite the surface of the operation portion 206 to which the insertion portion 202 is connected. The operation knob 203 is provided on a right side surface of the operation portion 206 when the surface to which the insertion portion 202 is connected is defined as the bottom surface and when the surface of the operation portion 206 having the electric switch 204 is viewed from the surface to which the universal cord 207 is connected.

As shown in FIG. 13, the signal wire 221, comprising two cable wires each having one end connected to the electric connector 242, is placed in the universal cord 207. The other end of each of the two signal wires 221 is connected to the FPC 219 and extends into the operation portion 206. The FPC 219 has a contact portion 219a for connection to a connector 225 of a connection member 232 described below. The contact portion 219a is electrically connected to a plurality of conductor wires of the signal wire 221.

As shown in FIG. 15, the plurality of electric switches 205 are projectively fixed to an armor member of the operation portion 206 in order to operate an external instrument 241 such as a video processor. Further, an FPC 228 is located in the vicinity of the electric switches 205 and has a planar portion substantially parallel to the surface of the operation portion 206 having the electric switches 205. Signal cables 227 extending from the electric switches 205 into the operation portion 206 are soldered to the FPC 228. The FPC 228 has an elongate extending portion at one end thereof which extends like a band. A contact portion 228a is provided at a distal end of the extending portion for connection to a connector 229 of the connection member 232 described below. The contact portion 228a is disposed on a surface of the FPC 228 which is opposite to the surface where the electric switches 205 are provided. The extending portion of the FPC 228 is bent through 90° so that the surface of the extending portion having the contact portion 228a lies substantially parallel and back to back to the surface of the operation portion 206 on which the electric switch 204 is provided. As shown in FIG. 15, the extending portion of the FPC 228 is oriented to the inside of the operation portion 206, in the direction of the insertion portion 202 being connected. Furthermore, the FPC 228 has a circuit that electrically connects the signal cable 227 to the contact portion 228a.

Further, the electric switch 204 is projectively fixed to an armor member of the operation portion 206 in order to operate the external instrument 241 such as a video processor. Inside the operation portion 206, the electric switch 204 is mounted directly on the FPC 230, located substantially parallel to the surface of the operation portion 206 having the electric switch 204. The electric switch 204 and the FPC 230 are integrally fixed to the armor member of the operation portion 206. The FPC 230 has an elongate extending portion at one end which extends like a band. The extending portion has a contact portion 230a for connection to a connector 231 of the connection member 232 described below. The contact portion 230a is provided on the surface of the FPC 230 on which the electric switch 204 is mounted. The extending portion of the FPC 230 is bent through 90° so that the surface of the extending portion having the contact portion 230a crosses, at right angles, the surface of the operation portion 206 having the electric switch 204 and the rear of the surface of the extending portion having the contact portion 230a faces the surface of the operation portion 206 having the electric switches 205.

Thus, as shown in FIG. 15, the extending portion of the FPC 230 faces toward the interior of the operation portion 206 in the direction of the universal cord 207 being connected. Furthermore, the FPC 230 has a circuit that electrically connects the electric switch 204 to the contact portion 230a.

On the other hand, as shown in FIG. 16, the connection member 232 which is composed of FPC on which connecters 225, 229 and 231 are mounted are arranged inside the operation portion 206: the contact portion 219a of the FPC 219 is connected to the connector 225, the contact portion 228a of the FPC 228 is connected to the connector 229, and the contact portion 230a of the FPC 230 is connected to the connector 231. The connectors 225, 229, and 231 have releasing mechanisms 225a, 229a, and 231a, respectively. The connection member 232 has rigid portions 232a formed by sticking rigid plate-like members to the back surface of the respective areas of the connection member 232 on which the connectors 225, 229, and 231 are mounted. Further, the areas of the connection member 232 other than the rigid portions 232a comprise flexible portions 232b. The connection member 232 can be bent at the points of the flexible portions 232b. Bending the connection member 232 at the points of the flexible portions 232b makes it easy to dispose the connection member 232 folded into a predetermined shape, inside the operation portion 206.

Furthermore, the connection member 232 has a circuit that electrically connects the connectors 225, 229, and 231 together. As shown in FIG. 16, according to the present embodiment, the connection member 232 has the three substantially rectangular rigid portions 232a, which are connected together in series via the flexible portions 232b. The connectors 225, 229, and 231 are mounted on the three respective rigid portions 232a. The connectors 225, 229, and 231 are mounted on the connection member 232 so that when the FPCs 219, 228, and 230 are connected to the openings in the connectors 225, 229, and 231, the surfaces of the contact portions of the FPCs 219, 228, and 230 lie parallel to the surface of the connection member 232. Further, the connectors 225, 229, and 231 are mounted so that the opening directions of the openings in the connectors 225, 229, and 231 are the same and orthogonal to the direction in which the rigid portions 232a are arranged. The connectors 225, 229, and 231 are mounted on the connection member 232 in order of the connectors 225, 231, 229 from the left as viewed from a direction opposite to the openings with the connection member placed so that the surface thereof with the connectors 225, 229, and 231 mounted thereon faces upward.

As shown in FIG. 17, inside the operation portion 206, the FPCs 219, 228, and 230 are inserted into the openings in the connectors 225, 229, and 231, respectively, and the releasing mechanisms 225a, 229a, and 231a are operated to catch the FPCs 219, 228, and 230. This operation electrically connects the electric switches 204 and 205 via the connection member 232 to the signal lines 221 connected to the electric connector 242. The operation portion signal line is composed of the signal wire 221, the FPCs 228 and 230, and the connection member 232.

Now, with reference to FIG. 17, description will be given of a method of arranging the FPCs 219, 228, and 230 inside the operation portion 206 when connecting the FPCs 219, 228, and 230 to the connection member 232.

First, the connection member 232 is temporarily placed inside the operation portion 206 so that the surface of the connection member 232 on which the connectors are mounted faces a direction opposite to the surface of the operation portion 206 having the operation knob 203 and so that the openings of the mounted connectors face opposite to the surface of the operation portion 206 to which the universal cord 207 is connected.

The FPC 219 is inserted into the connector 225 so that the surface of the FPC 219 having the contact portion 219a faces opposite to the surface of the operation portion 206 having the operation knob 203.

Further, the extending portion of the FPC 228 with the distal end of the contact portion 228a thereof extending in the direction of the insertion portion 202 being connected is bent through 90° with the surface of the FPC 228 having the contact portion 228a located inside to direct the distal end of the extending portion in the direction of the universal cord 207 being connected. Moreover, the extending portion of the FPC 228 is twisted 90° so that the surface of the FPC 228 having the contact portion 228a faces a direction opposite to that of the operation portion 206 having the operation knob 203. Subsequently, the extending portion of the FPC 228 is bent back through 180° in the vicinity of the contact portion 228a so that the surface of the FPC 228 having the contact portion 228a is located inside. Thus, the surface of the FPC 228 having the contact portion 228a lies opposite to the surface of the operation portion 206 having the operation knob 203. Moreover, the connection member 232 is placed inside the portion of the FPC 228 at which the extending portion thereof has been bent back through 180°. The contact portion 228a is then inserted into the connector 229 with the extending portion of the FPC 228 extending over and along the surface of the connection member 232 on which the connector 229 is not mounted, to the surface of the connection member 232 on which the connector 229 is mounted.

The above operation allows the FPC 228 to be inserted into the connector 229 with the surface of the FPC 228 having the contact portion 228a facing the surface of the operation portion having the operation knob 203.

Furthermore, the extending portion of the FPC 230 with the distal end of the contact portion 230a thereof extending toward the side of the operation portion 206 to which the universal cord 207 is connected is twisted through 90° with the surface of the FPC 230 having the contact portion 230a facing opposite to the surface of the operation portion 206 having the operation knob 203. Subsequently, the extending portion of the FPC 230 is bent back through 180° in the vicinity of the contact portion 230a so that the surface of the FPC 230 having the contact portion 230a is located inside. Thus, the surface of the FPC 230 having the contact portion 230a faces opposite to the surface of the operation portion 206 having the operation knob 203. Moreover, the connection member 232 is placed inside the portion of the FPC 230 at which the extending portion thereof has been bent back through 180°. The contact portion 230a is then inserted into the connector 231 with the extending portion of the FPC 230 extending over and along the surface of the connection member 232 on which the connector 231 is not mounted, to the surface of the connection member 232 on which the connector 231 is mounted.

The above operation allows the FPC 230 to be inserted into the connector 231 with the surface of the FPC 230 having the contact portion 230a facing the surface of the operation portion having the operation knob 203.

With the above method, inserting the contact portions 219a, 228a, and 230a into the respective connectors enables FPCs 219, 228, and 230 to be untwisted when the connection member 232 is housed in a metal housing 234 described below.

The present embodiment makes the connections such that the contact portions 219a, 228a, and 230a face the surface of the connection member on which the connectors are mounted. However, each contact portion may be provided on the surface of the corresponding FPC opposite to that described above depending on the requirement for the connector.

Further, as shown in FIG. 17, display portions TD1 and TD2 that displays characters or symbols (numbers 1, 2, 3 in FIG. 17) indicating combinations of the connectors 225, 229, and 231 of the connection member 232 and the contact portions of the FPCs 219, 228, and 230 are provided in the vicinity of the each connector and in the vicinity of each contact portion, respectively. The display makes it possible to visually easily confirm the state of the connections, enabling the prevention of the misconnection between each connector and the corresponding FPC.

As shown in FIGS. 18 and 19, a member 233 electrically connected to a ground terminal of the external instrument is located inside the operation portion 206. The metal housing 234 is fixed to the member 233 using a conductive screw 235. The housing 234 is formed like a rectangular parallelepiped box by bending a metal plate. Further, an opening through which the connection member 232 is inserted and housed is provided in the housing 234 with a surface lying opposite to the surface of the operation portion 206 having the electric switch 204. The connection member 232 with the FPCs 219, 228, and 230 connected thereto is folded into a substantial Z shape at the flexible portions 232b and then inserted and housed in the opening. At this time, as shown in FIG. 18, the connection member 232 is folded with the connectors 229 and 231 located inside the bent back portions and with the connector 225 facing the outward direction. As shown in FIG. 19, the connection member 232 is housed in the opening so that the opening direction of the openings in the connectors 225, 229, and 231 is the same as that of the opening formed in the metal housing 234. Further, at this time, FPCs 219, 228, and 230 are inserted into the openings in the connectors 225, 229, and 231, respectively, with slight length allowances.

Thus housing the connection member in the electrically grounded metal housing enables the connection portions of the signal wires to be shielded. This enables a reduction in noise radiated to the exterior from the signal wire connection portion, for which EMC measures have not hitherto been taken, and in external noise entering the signal wire connection portion.

Further, as shown in FIG. 19, the bent FPCs 219, 228, and 230 are inserted into the openings in the connectors 225, 229, and 231, respectively, with length allowances. Thus, the force exerted by the bent FPCs 219, 228, and 230 for restoration biases the distal end portions of the FPCs 219, 228, and 230 in the direction in which the FPCs 219, 228, and 230 are inserted into the openings in the connectors 225, 229, and 231, respectively. This makes it difficult to pull out the distal end portions of the FPCs 219, 228, and 230 from the openings in the connectors 225, 229, and 231, respectively.

Further, the biasing force of the FPCs 219, 228, and 230 acting toward the interior of the housing 234 causes the connection member 232 to be inserted until the connection member 232 abuts against the inner wall surface of the opening, for fixation. This makes it difficult to slip out the connection member 232 from the housing 234. Furthermore, the connection member 232 bent into a Z shape is pressed against the internal side wall surface of the housing 234 by the restoring force of the connection member itself. Thus, the connection member 232 is unlikely to slip out of the housing 234.

Therefore, while the connecting portion of the signal wires by the conventional connectors are made reliable by means of fixture with an adhesive, for example, an epoxy-based adhesive, the present embodiment can achieve reliable connections without applying any adhesive. This enables a reduction in the time required for assembly and disassembly operations and in the number of tools required.

Figure 20:
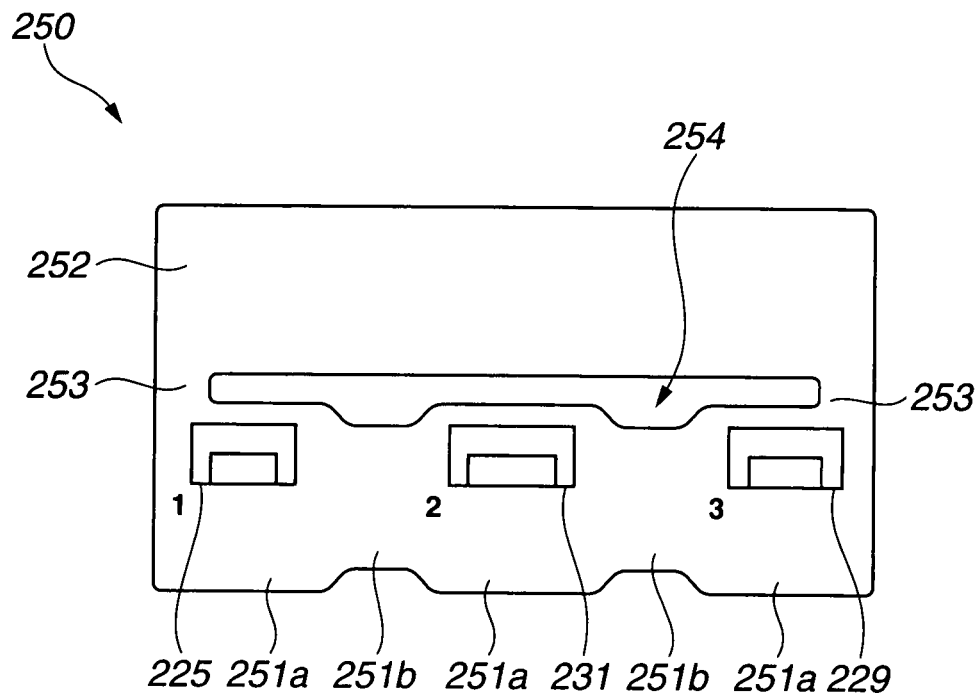
FIG. 20 is a plan view showing a variation of the connection member in accordance with the second embodiment.
Figure 21:
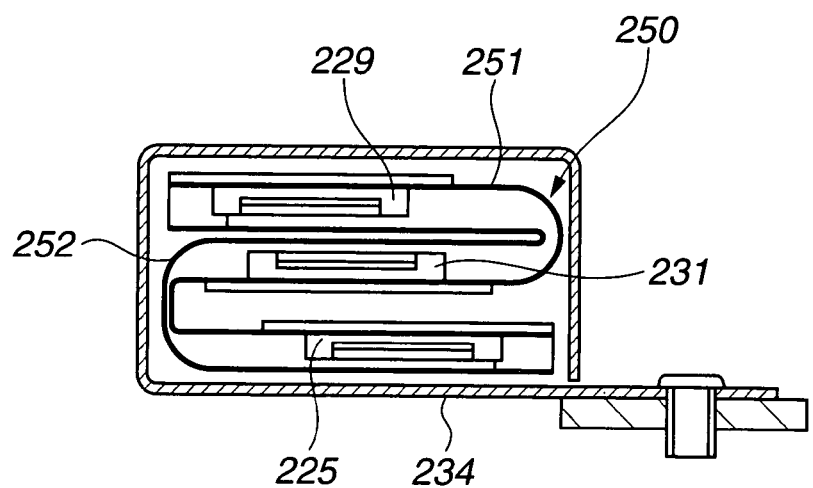
FIG. 21 is a partial sectional view showing how the connection member in accordance with the second embodiment is housed in the metal housing.

Here, with reference to FIGS. 20 and 21, description will be given of a variation of the connection member 232 shown in FIG. 16. FIG. 20 is a plan view of a connection member 250. FIG. 21 is a partial sectional view showing how the connection member 250 is housed in the metal housing 234.

As shown in FIG. 20, the connection member 250 is composed of an FPC divided into two parts, a connector mounting portion 251 and an insulating portion 252, in a latitudinal direction by a slit 254 which is substantially rectangular and which is formed along a central axis in a longitudinal direction. That is, the connector mounting portion 251 and the insulating portion 252, each of which is rectangular, are connected in parallel at the opposite ends in the longitudinal direction via connection portions 253 formed at the opposite ends of the slid 254.

The connector mounting portion 251 has a configuration equivalent to that of the connection member 232, shown in FIG. 16, and includes three substantially rectangular rigid portions 251a connected in series via flexible portions 251b. The three rigid portions 251 a of the connector mounting portion 251 are equipped with the connector 225, to which the contact portion 219a of the FPC 219 is connected, the connector 229, to which the contact portion 228a of the FPC 228 is connected, and the connector 231, to which the contact portion 230a of the FPC 230 is connected. The connectors 225, 229, and 231 are mounted so that the opening direction of the respective openings is orthogonal to the arranging direction of the rigid portions 232a and opposite to the insulating portion 252. The connectors 225, 229, and 231 are mounted on the connection member 250 in order of the connectors 225, 231, and 229 from the left as viewed from a direction opposite to the openings when the surface of the connection member 250 on which the connectors 225, 231, and 229 are mounted is set to face the upward direction.

On the other hand, the insulating portion 252 is entirely flexible and is formed of polyimide, which constitutes FPC and offers an insulating property.

As shown in FIG. 20, the connection member 250 is housed in the housing 234, provided in the operation portion 206 as described below. First, the connection member 250 is bent at the connection portions 253 so that the surface of the connection member 250 on which the connectors 225, 229, and 231 are mounted is located inside. Subsequently, the connection member 250 is bent into a Z shape at the flexible portions 251b so that the surface of the connection member 250 on which the connector 225 is mounted faces the surface of the connection member 250 on which the connector 231 is mounted, while the surface of the connection member 250 on which the connector 251 is mounted faces the outward direction. The connection member 250 bent into a Z shape is inserted and housed in the housing 234 with the FPCs 219, 228, and 230 being connected thereto.

If the FPCs 219, 228, and 230 are connected via the connection member 250 in accordance with the present variation, the surface of the connection members 250 on which the connectors 225, 229, and 231 are mounted is covered with an insulating portion 252, offering an insulating property, as shown in FIG. 20. That is, the insulating portion 252 is interposed between the connector 225 and the connector 231 and also the insulating portion 252 is interposed between the connector 229 and an inner peripheral surface of the housing 234. Thus, the connection member 250 in accordance with the variation electrically reliably insulates the connector 229 from the connector 231 and the connector 225 from the housing 234. This improves the reliability of the electronic endoscope 201. Furthermore, it is unnecessary to use separate members to electrically insulate the connector 229 from the connector 231 and the connector 225 from the housing 234. This enables a reduction in the number of the parts of the electronic endoscope 201 and in the number of assembly steps.

Moreover, the connection member 250 in accordance with the present variation is bent at the connection portions 253 and then the connection member 250 bent into a Z shape is housed in the housing 234. Thus, the connection member 250 composed of the FPC attempts to expand in a direction in which the connection member 250 restores from the state where it is bent inside the housing 234. Consequently, the connection member 250 is pressed against the inner wall surface of the housing 234 and fixed to the housing 234 by the restoring force of the connection member itself. Thus, the present variation enables the connection member 250 to be fixed to the inside of the housing 234 without using any adhesive. This allows a reduction in the number of assembly steps.

Further, for the connection member 250 in accordance with the present variation, it is only necessary that both the front and back surfaces of the insulating portion 252 are covered with an insulating material. For example, the insulating portion 252 may be composed of a copper foil, a conductive material, which is connected to a ground potential terminal of the connector 225, 229, or 231 and the opposite surfaces of which are covered with polyimide. The thus configured connection member 250 makes it possible to electrically insulate the connector 225 from the connector 231 and the connector 229 from the housing 234 and to shield the connectors from one another. This improves electromagnetic compatibility.

The electronic endoscope in accordance with the second embodiment exerts the following effects. To replace any parts of the electronic endoscope in accordance with the conventional art for repair or the like, it was necessary to disconnect the signal wire from the electric connector, take required action for the repair such as parts replacement, and then connect the signal wire back to the electric connector. However, according to the present embodiment, when the image pickup portion 211 including the CCD from the electronic endoscope 201 owing to, for example, defective images is desired to be removed, the signal wire 215 connected to the image pickup portion 211 can be removed from the electronic endoscope 201 by removing the signal wire 215 connected to the image pickup portion 211 from the connector 217 in the operation portion 206. Thus, the operation of removing the image pickup portion 211 from the electronic endoscope 201 does not require the disassembly of the electric connector 242 and can thus be easily performed in a short time.

Further, when the electric switch 204 or 205 is desired to be replaced from the electronic endoscope 201 owing to a defect in the switch 204 or 205, removal of the electric switch 204 or 205 from the electronic endoscope 201 can be achieved by removing the FPC 228 or 230 connected to the electric switch 204 or 205, respectively, from the connector 229 or 231, respectively, of the connection member 232. Thus, the operation of removing the electric switch 204 or 205 from the electronic endoscope 201 does not require the disassembly of the electric connector 242 and can thus be easily performed in a short time.

Moreover, there has been a tendency to reduce the size and weight of connectors for connection of the signal wires inside the electronic endoscope main body; for example, microconnectors have been often used for this purpose. Repeated installation and removal of small, light connectors is likely to reduce the force of the releasing mechanism required to fixedly catch the flexible circuit board. Thus, maintaining the reliability of connections of signal wires using connectors required the replacement of a connector having a releasing mechanism with a reduced fixation strength with a new one. For example, to replace a connector provided at an end of a signal wire, the signal wire to which the connector is connected must be removed from the electronic endoscope main body. To remove any signal wire from the electronic endoscope main body, it is necessary to perform the operation of pulling out the build-in parts including the signal wire in the universal cord and then disconnect the signal wire from the corresponding electric connector provided in the scope connector. Thus, the connector replacing operation disadvantageously required a long time and dedicated tools and jigs. However, according to the present embodiment, the connectors are provided on the independent connection members 223 and 232, via which the signal wires are connected together. This enables any of the connectors to be replaced with a new one easily in a short time.

More specifically, according to the present invention, if the releasing mechanism for any of the connectors to which the signal wires are fixedly connected exhibits a reduced fixation strength and that connector thus needs to be replaced with a new one, the connector replacing operation is finished by removing the connection member on which the connector to be replaced is mounted, and replacing it with a new one. Since the connection member is connected to each signal wire via the corresponding connector, the connection member can be removed by manually operating the releasing mechanism for the connector. Thus, the present embodiment makes it possible to manually perform the connector replacing operation conventionally required disassembling the scope connector and then removing solders without the need for tools. This enables the connector replacing operation to be completed in a shorter operation time and with fewer tools than the conventional art.

Further, according to the present embodiment, the connectors are provided only on the independent connection member, preventing the signal wires from being affected by the repeated connector replacing operation, that is, the repeated replacement of the connection member. The conventional art required the cutting the distal ends of the signal wires to the same length for connector replacement. However, the present embodiment prevents the signal wires from being shortened in the connector replacement operation, eliminating the need to replace the entire signal wire, which is not the original replacement target.

The above described endoscope is one embodiment of the electronic endoscope in accordance with the present invention. The specific contents of the embodiment can be changed without departing from the spirits of the present invention. For example, the following aspects are possible.

According to the present embodiment, the FPCs 216 and 218 are provided at the one ends of the signal wires 215 and 220, respectively, in order to connect the signal wires 215 and 220 to the connectors 217 and 222, respectively. However, the connection end of each signal wire may have the configuration only to be able to connect to the connector. For example, a rigid circuit board may be provided at the signal wire end or a cable may be used which is formed by bundling conductor wires into a band.

Moreover, according to the present embodiment, the scope connector 208 proximal ends of the signal wires 220 and 221 are soldered directly to the electric connector 242. However, the signal wires 220 and 221 may be freely installed in and removed from the electric connector 242 by providing FPCs at the scope connector 208 side proximal ends similar to the distal ends and providing connectors on the electric connector 242. This configuration enables the signal wires 220 and 221 to be more easily replaced in a shorter time than the conventional configuration.

Further, according to the present embodiment, each of the connection members 223 and 232 is configured such that the connectors are mounted on the FPC, a flexible circuit board. However, the connectors may be mounted on a rigid circuit board or provided at the opposite ends of a cable having a signal wire as long as the corresponding signal wires can be electrically connected.

Furthermore, the present embodiment varies the fitting width between the FPC and the connector depending on the combination in order to prevent the possible misconnection between the FPC and the connector. However, possible misassembly can also be prevented by varying the thickness of the fitting portion between the FPC and the connector depending on the combination.

Moreover, the present embodiment prevents the possible misconnection by clearly indicating the combinations with the characters or symbols in the vicinity of the connectors of the connection member and in the vicinity of the connection portions of FPCs. However, possible mis-combinations can also be prevented by using colors to clearly indicate the combinations.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric connector for an endoscope provided on a connection cable extending from an operation portion of the endoscope, the electric connector electrically connecting a cable wire extending from the operation portion of the endoscope with an external instrument for use in combination with the endoscope, the electric connector comprising:
   a circuit board comprising:
      a connection member that is electrically connected to the external instrument;
      a connector to which a cable wire connector connected to an end portion of the cable wire is releasably connected
      a first circuit board portion having a hole portion formed therein;
      a second circuit board portion; and
      a flexible circuit board portion that is bent so that the first circuit board portion and the second circuit board portion at least partly overlap each other as viewed from a direction substantially orthogonal to a surface of the first circuit board portion; and
   the connection member comprises:
      a first conductor connected to the second circuit board portion and configured to be inserted through the hole portion formed in the first circuit board portion in the arrangement where the first circuit board portion and the second circuit board portion at least partly overlap each other as viewed from a direction substantially orthogonal to a surface of the first circuit board portion; and
      a second conductor connected to the first circuit board portion, wherein the longitudinal axis of the second conductor and the longitudinal axis of the first conductor are substantially parallel.

2. The electric connector for the endoscope according to claim 1, wherein a proximal end portion of the cable wire is electrically connected to a component, having a predetermined function, provided in at least one of an insertion portion and the operation portion of the endoscope.

3. An endoscope comprising:
an insertion portion;
an operation portion provided at a proximal end of the insertion portion;
a connection cable extending from the operation portion, the connection cable comprising an electric connector for connecting to an external instrument;
a cable wire extending from the operation portion and inserted through the connection cable, the cable wire comprising a proximal end portion electrically connected to a component, having a predetermined function, provided in at least one of the insertion portion and the operation portion;
a cable wire connector provided at an end portion of the cable wire;
the electric connector of the connection cable comprising:
a circuit board comprising:
a connection member electrically connected to the external instrument and
a connector to which the cable wire connector is releasably electrically connected;
wherein:
the cable wire connector comprises:
a cable wire connection portion to which the cable wire is electrically connected; and
a connection terminal portion that is releasably connected to the connector on the circuit board, and
the cable wire connection portion and the connection terminal portion are integrally formed using a flexible circuit board.

4. The endoscope according to claim 3, wherein the connection terminal portion of the cable wire connector comprises a guide portion that guides a direction for connection to the connector on the circuit board.

5. An endoscope comprising:
an insertion portion;
an operation portion provided at a proximal end of the insertion portion;
a connection cable extending from the operation portion, the connection cable comprising an electric connector for connecting to an external instrument;
a cable wire extending from the operation portion and inserted through the connection cable, the cable wire comprising a proximal end portion electrically connected to a component, having a predetermined function, provided in at least one of the insertion portion and the operation portion;
a cable wire connector provided at an end portion of the cable wire;
the electric connector of the connection cable comprising:
a circuit board comprising:
a connection member electrically connected to the external instrument; and
a connector to which the cable wire connector is releasably electrically connected;
wherein:
the cable wire connector is formed substantially like a T shape, and comprises:

a cable wire connection portion on which connection lands to which a plurality of signal wires of the cable wire are connected are formed;
a connection terminal portion formed to extend substantially orthogonally from the cable wire connection portion and releasably connected to the connector on the circuit board; and
holding portions provided at opposite ends of the cable wire connection portion to hold the cable wire connection portion in a substantially cylindrical shape, and
the cable wire connection portion, the connection terminal portion, and the holding portions are integrally formed using a flexible circuit board.

6. The endoscope according to claim 5, wherein the connection terminal portion of the cable wire connector comprises a guide portion that guides a direction for connection to the connector on the circuit board.

7. An endoscope comprising:
an insertion portion;
an operation portion provided at a proximal end of the insertion portion;
a connection cable extending from the operation portion, the connection cable comprising an electric connector for connecting to an external instrument;
a cable wire extending from the operation portion and inserted through the connection cable, the cable wire comprising a proximal end portion electrically connected to a component, having a predetermined function, provided in at least one of the insertion portion and the operation portion;
a cable wire connector provided at an end portion of the cable wire;
the electric connector of the connection cable comprising:
a circuit board comprising:
a connection member electrically connected to the external instrument; and
a connector to which the cable wire connector is releasably electrically connected;
wherein:
the cable wire connector is formed substantially like a rectangle, and comprises:
a cable wire connection portion to which the cable wire is connected;
a connection terminal portion that is releasably connected to the connector on the circuit board; and
a locking portion formed around a periphery of the connection terminal portion, and
the cable wire connection portion, the connection terminal portion, and the locking portion are integrally formed using a flexible circuit board.

8. A method for assembling an electric connector which is provided on a connection cable extending from an operation portion of an endoscope and which comprises a first circuit board portion and a second circuit board portion and comprising a flexible circuit board bent so that the first circuit board portion and the second circuit board portion at least partly overlap each other as viewed from a direction orthogonal to a surface of the first circuit board portion, the circuit board having a connection member electrically connected to an external instrument and a connector to which a cable wire connector connected to an end portion of a cable wire extending from the operation portion of the endoscope is releasably connected, the method comprising:
a first circuit board portion connecting step of inserting the connection member into a hole portion formed in the first circuit board portion to connect the connection member to a land provided in a periphery of the hole portion of the first circuit board portion;

a second circuit board portion connecting step of bending the circuit board to insert the connection member projecting from the first circuit board portion into the hole portion formed in the second circuit board portion to connect the connection member to the land provided in the periphery of the hole portion of the second circuit board portion; and a cable wire connector installing step of installing the cable wire connector in the connector of the circuit board.

9. The method for assembling an electric connector according to claim 8, wherein in the first circuit board portion connecting step, the connection of the connection member to the land is performed first in a central portion of the circuit board portion and then in an outer edge portion of the first circuit board portion.

10. The method for assembling an electric connector according to claim 8, wherein the connection member has a solid wire terminal member and a coaxial terminal member, and in the first circuit board portion connecting step, the connection of the connection member to the land is performed by first connecting the solid wire terminal member to the land and then connecting the coaxial terminal member to the land.

11. An endoscope comprising:
an insertion portion;
an operation portion provided at a proximal end portion of the insertion portion; and
a connection cable connected to the operation portion, the connection cable comprising:
an electric connector at a proximal end;
a first cable wire having a first end connected to the electric connector and extending into the operation portion;
a second cable wire having a first end connected to an image pickup portion provided in the insertion portion or an electric switch provided on the operation portion, the second cable wire extending into the operation portion; and
a connection member comprising:
a flexible circuit board; and
a plurality of connectors mounted on the flexible circuit board, wherein a second end of the first cable wire and a second end of the second cable wire are electrically and releasably connected to the plurality of connectors; and
a conductive housing within which the connection member is arranged.

12. The endoscope according to claim 11, wherein the flexible circuit board comprises:
a plurality of rigid portions on which the plurality of connectors are mounted; and
a flexible portion, exhibiting flexibility, provided between the rigid portions.

13. The endoscope according to claim 11, wherein a plurality of display portions displaying characters or symbols are provided in the vicinity of the plurality of connectors on the connection member and in the vicinity of the second end of the first cable wire and the second end of the second cable wire.

14. The endoscope according to claim 11, wherein the plurality of connectors on the connection member and the second end of the first cable wire and the second end of the second cable wire which are connected to the respective connectors on the connection member have different fitting widths or different colors depending on a combination of the connector and the cable wire.

15. The endoscope according to claim 11, wherein the flexible circuit board is housed in the conductive housing so that connection portions between the second end of the first cable wire and the second end the second cable wire and the connection member abut against an inner wall of the conductive housing.

16. The endoscope according to claim 11, wherein the connection member further comprises:
an insulating portion formed of a material having a surface offering an electric insulating property.

* * * * *

UNITED STATES PATENT AND TRADEMARK OFFICE
CERTIFICATE OF CORRECTION

| | | Page 1 of 1 |
|---|---|---|
| PATENT NO. | : 8,075,477 B2 | |
| APPLICATION NO. | : 11/827752 | |
| DATED | : December 13, 2011 | |
| INVENTOR(S) | : Naohiro Nakamura et al. | |

It is certified that error appears in the above-identified patent and that said Letters Patent is hereby corrected as shown below:

In The Claims:

Column 38, Line 48 (claim 1, line 12): It reads "nected"
                                      It should read --nected;--

Column 39, Line 27 (claim 3, line 19): It reads "external instrument and"
                                      It should read --external instrument; and--

Signed and Sealed this
Fifth Day of June, 2012

David J. Kappos
*Director of the United States Patent and Trademark Office*